US006300087B1

(12) United States Patent
Bard et al.

(10) Patent No.: US 6,300,087 B1
(45) Date of Patent: *Oct. 9, 2001

(54) DNA ENCODING A HUMAN SEROTONIN RECEPTOR (5-HT$_{4B}$) AND USES THEREOF

(75) Inventors: Jonathan A. Bard, Doylestown, PA (US); Theresa Branchek; Richard L. Weinshank, both of Teaneck, NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/450,797

(22) Filed: Nov. 29, 1999

Related U.S. Application Data

(62) Continuation of application No. 09/332,837, filed on Jun. 14, 1999, which is a continuation of application No. 08/157,185, filed as application No. PCT/US93/10553 on Oct. 29, 1993, now Pat. No. 5,985,585, which is a continuation-in-part of application No. 07/971,690, filed on Nov. 3, 1992, now abandoned, and a continuation-in-part of application No. 08/281,526, filed on Jul. 27, 1994, now Pat. No. 6,083,749.

(51) Int. Cl.$^7$ ............................ C12N 15/18; G01N 33/00

(52) U.S. Cl. ......................... 435/7.21; 435/325; 435/356; 435/357; 435/358; 435/365

(58) Field of Search .................................. 435/7.21, 69.1, 435/325, 356, 357, 358, 365

(56) References Cited

U.S. PATENT DOCUMENTS

| | | |
|---|---|---|
| 4,985,352 | 1/1991 | Julius et al. . |
| 5,155,218 | 10/1992 | Weinshank et al. . |
| 5,225,543 | 7/1993 | Eppler et al. . |
| 5,360,735 | 11/1994 | Weinshank et al. . |
| 5,914,236 | 6/1999 | Monsma et al. . |
| 5,985,585 | * 11/1999 | Bard et al. . |

FOREIGN PATENT DOCUMENTS

| | | |
|---|---|---|
| 1208146 | 7/1986 | (CA) . |
| 9106648 | 5/1991 | (WO) . |
| 9113979 | 9/1991 | (WO) . |
| 9117174 | 11/1991 | (WO) . |
| 9311147 | 6/1993 | (WO) . |
| 9314201 | 7/1993 | (WO) . |
| 9401555 | 1/1994 | (WO) . |
| 9401556 | 1/1994 | (WO) . |
| 9410311 | 5/1994 | (WO) . |
| 9416067 | 7/1994 | (WO) . |
| 9421670 | 9/1994 | (WO) . |

OTHER PUBLICATIONS

Bertin, B., et al., Functional Expression of the Human Serotonin 5–HT$_{1A}$ Receptor in *Escherichia coli*. J. Biol. Chem. 267(12): 8200–8206 (Apr. 25, 1992).

Schwinn, D.A., et al., "Molecular Cloning and Expression of the cDNA of a Novel α1–Adrenergic Receptor Subtype", Journal of Biological Chemistry 265(14):8183–8189 (1990).

Strosberg, J., et al., Functional expression of receptors in microorganisms. TiPS 13: 95–98 (Mar., 1992).

Bockaert, J., et al., "Pharmacological Characterization of 5–Hydroxytryptamine$_4$ (5–HT$_4$) Receptors Positively Coupled to Adenylate Cyclase in Adult Guinea Pig Hippocampal Membranes: Effect of Substituted Benzamide Derivatives," Amer. Soc. Pharm. Exper. Ther. 1989 37: 408–411.

Dumuis, A., et al., "A Nonclassical 5–Hydroxytryptamine Receptor Positively Coupled with Adenylate Cyclase in the Central Nervous System," Amer. Soc. Pharm. Exper. Ther. 1988 34: 880–887.

El Mestikawy, et al., "The 5–HT$_{1A}$ Receptor: An Overview of Recent Advances," Neurochemical Research 1991 16:(1):1–10.

Hen, R., "Of Mice And Flies: Commonalities Among 5–HT Receptors", *Trends in Pharmacological Sciences* (Apr. 1992) 13: 160–165.

Kobilka, B.K., et al., "An intronless gene encoding a potential member of the family of receptors coupled to guanine nucleotide regulatory proteins," Nature 1987 329: 75–79.

Lovenberg, et al., "A Novel Adenylyl Cyclase–Activating Serotonin Receptor (5–HT$_7$) Implicated In The Regulation Of Mammalian Circadian Rhythms" *Neuron*,(1993) 11:449–458.

Martin, G.R., et al., "Operational Characterization of a 5–HT Receptor Mediating Direct Vascular Relaxation: Identity with the 5–HT7 Receptor?" Proc. Brit. Pharm. Soc. Dec. 1994, p. 221.

Meyerhof, W., et al., "A Novel Rat Serotonin Receptor: primary structure, pharmacology, and expression pattern in distinct brain regions," DNA & Cell Biology 12(5):401–409 (Jun. 1993).

(List continued on next page.)

Primary Examiner—Marianne P. Allen
(74) Attorney, Agent, or Firm—Christopher C. Dunham; Cooper & Dunham LLP

(57) ABSTRACT

This invention provides an isolated nucleic acid molecule encoding a mammalian 5-HT$_{4B}$ receptor and an isolated nucleic acid molecule encoding a human 5-HT$_{4B}$ receptor, an isolated protein which is mammalian 5-HT$_{4B}$ receptor, vectors comprising an isolated nucleic acid molecule encoding a mammalian 5-HT$_{4B}$ receptor, vectors comprising an isolated nucleic acid molecule encoding a human 5-HT$_{4B}$ receptor, mammalian cells comprising such vectors, antibodies directed to the 5-HT$_{4B}$ receptor, nucleic acid probes useful for detecting nucleic acid encoding a mammalian or human 5-HT$_{4B}$ receptor, antisense oligonucleotides complementary to any sequences of a nucleic acid molecule which encodes a mammalian or human 5-HT$_{4B}$ receptor, pharmaceutical compounds related to the human 5-HT$_{4B}$ receptor. This invention further provides methods for determining ligand binding, detecting expression, drug screening, and treatments for alleviating abnormalities associated with a human 5-HT$_{4B}$ receptor.

12 Claims, 12 Drawing Sheets

OTHER PUBLICATIONS

Figure 4:
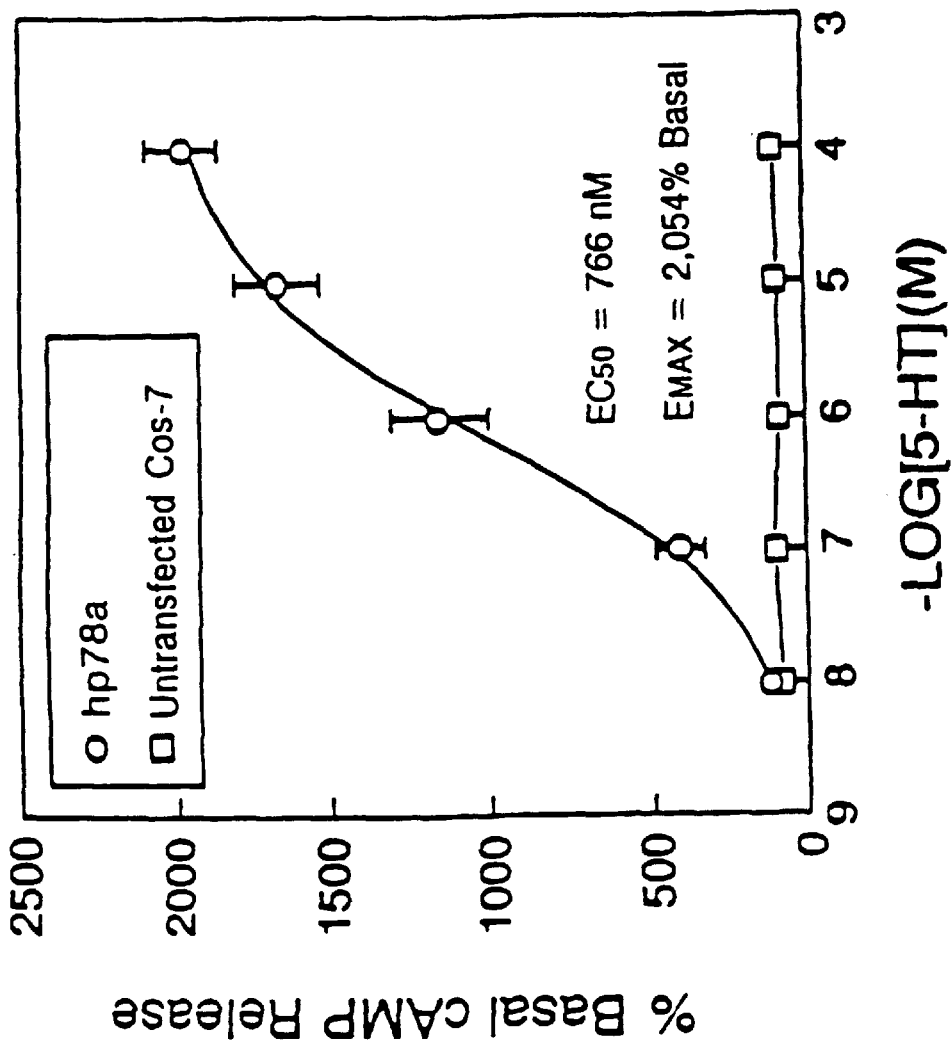

New England Biolabs Catalog, 1990–1991, p. 48.

NTIS Publication No. PB93–139335, Sibley, D.R., et al., Apr. 1, 1993.

Roth, B.L., et al., "Binding of Typical and Atypical Antipsychotic Agents to 5–Hydroxytryptamine–6 and 5–Hydroxytryptamine–7 Receptors," J. Pharm. Exp. Ther. 1994 268(3):1403–1410.

Ruat, et al., "Molecular Cloning, Characterization, And Localization Of A High–Affinity Serotonin Receptor (5–$HT_7$) Activating cAMP Formation" *PNAS(USA)*, (1993) 90: 8457–8551.

Shen, et al., "Molecular Cloning And Expression of a 5–Hydroxytryptamine$_7$ Serotonin Receptor Subtype" *J. Biol. Chem.*, (1993) 268(24): 18200–18204.

Weinshank, R.L., et al., Molecular Analysis of Serotonin Receptor Subtypes. Langer, S.Z., et al (eds.): *Serotonin Receptor Subtypes: Pharmacological Significance and Clinical Implications*, Int. Acad. Biomed. Drug Res., Basel Karger 1992 1:1–12.

Witz, P., et al., "Cloning and Characterization of a Drosophila Serotonin Receptor that Activates Adenylate Cyclase," Proc. Natl. Acad. Sci. USA 1990 87u: 8940–8944.

* cited by examiner

FIGURE 1-1

```
     -21                -1                          20
-27  CCATGGGCAGCGGCCACACGGGCGGCCGATGATGGACGTTAACAGCAGCGGCCCCGAC   33
 -8                         M  M  D  V  N  S  S  G  R  P  D     11

40              60              80
 34  CTCTACGGGCACCTCCGCTCTTTCCTTCTGCCAGAAGTGGGGCGGGGCTGCCCGACTTG   93
 12   L  Y  G  H  L  R  S  F  L  L  P  E  V  G  R  G  L  P  D  L  31

100             120             140
 94  AGCCCCGACGGTGGCGCCGACCCGGTCGCCGGCTCCTGGGCGCCCACCTGCTGAGCGAG  153
 32   S  P  D  G  G  A  D  P  V  A  G  S  W  A  P  H  L  L  S  E  51

160             180             200
154  GTGACAGCCAGCCCGGCCCCACCTGGGACAATGCCTCCGGCTGTGGG  213
 52   V  T  A  S  P  A  P  T  W  D  A  P  P  D  N  A  S  G  C  G  71

220             240             260
214  GAACAGATCAACTACGGCAGAGTCGAGAAAGTTGTGATCGGCTCCATCCTGACGCTCATC  273
 72   E  Q  I  N  Y  G  R  V  E  K  V  V  I  G  S  I  L  T  L  I  91
```

FIGURE 1-2

```
274  ACGGCTGCTGACGATCGGGGGCAACTGCCTGGTGGTGATCTCCGTGTGCTTCGTCAAGAAG  333
 92   T  L  L  T  I  A  G  N  C  L  V  V  I  S  V  C  F  V  K  K   111

334  CTCCCGCCAGCCCTCCAACTACCTGATCGTGTCCCTGGCCCTGGCCGACCTCTCGGTGGCT  393
112   L  R  Q  P  S  N  Y  L  I  V  S  L  A  L  A  D  L  S  V  A   131

394  GTGGCGGTCATGCCCTTCGTCAGCGTCACCGACCTCATCGGGGGCAAGTGGATCTTTGGA  453
132   V  A  V  M  P  F  V  S  V  T  D  L  I  G  G  K  W  I  F  G   151

454  CACTTTTTCTGTAATGTCTTCATCGCCATGGACGTCATGTGCTGCACGGCCTCGATCATG  513
152   H  F  F  C  N  V  F  I  A  M  D  V  M  C  C  T  A  S  I  M   171

514  ACCCTGTGCGTGATCAGCATTGACAGGTACCTTGGGATCACAAGGCCCCTCACATACCCT  573
172   T  L  C  V  I  S  I  D  R  Y  L  G  I  T  R  P  L  T  Y  P   191
```

FIGURE 1-3

```
574  GTGAGGCAGAATGGGAAATGCATGGCCAAGATGATTCTCCGTCTGGCTTCTCTCCGCC        633
192   V  R  Q  N  G  K  C  M  A  K  M  I  L  S  V  W  L  L  S  A      211
              580              600              620

634  TCCATCACCTTACCTCCACTCTTTGGATGGGCTCAGAATGTAAATGATGATAAGGTGTGC       693
212   S  I  T  L  P  P  L  F  G  W  A  Q  N  V  N  D  D  K  V  C      231
              640              660              680

694  TTGATCAGCCAGGACTTTGGCTATACGATTTACTCTACCGCAGTGGCATTTTATATCCCC      753
232   L  I  S  Q  D  F  G  Y  T  I  Y  S  T  A  V  A  F  Y  I  P      251
              700              720              740

754  ATGTCCGTCATGCTTTTCATGTACTACCAGATTTACAAGGCTGCCAGGAAGAGTGCTGCC      813
252   M  S  V  M  L  F  M  Y  Y  Q  I  Y  K  A  A  R  K  S  A  A      271
              760              780              800

814  AAACACAAGTTTCCTGGCTTCCCTGAGTGGAGCCAGACAGCGTCATCGCCCTGAATGGC       873
272   K  H  K  F  P  G  F  P  R  V  E  P  D  S  V  I  A  L  N  G      291
              820              840              860

874  ATAGTGAAGCTGCAGAAGGAGGTGGAAGAGTGTGCAAACCTTTCGAGACTCCTCAAGCAT      933
292   I  V  K  L  Q  K  E  V  E  E  C  A  N  L  S  R  L  L  K  H      311
              880              900              920
```

FIGURE 1-4

```
                     940               960               980
934  GAAAGGAAAAACATCTCCATCTTTAAGCGAGAGAAAGCAGCCACCACCCTGGGGATC   993
312   E  R  K  N  I  S  I  F  K  R  E  Q  K  A  A  T  T  L  G  I   331

1000              1020              1040
994  ATCGTCGGGGCCTTTACCGTGTGCTGGCTGCCATTTTTCCTCCTCTGACAGCCAGACCC  1053
332   I  V  G  A  F  T  V  C  W  L  P  F  F  L  L  S  T  A  R  P   351

1060              1080              1100
1054 TTCATCTGTGGCACTTCCTGCAGCTGCATCCCACTGTGGGTGGAGAGGACATTTCTGTGG 1113
352   F  I  C  G  T  S  C  S  C  I  P  L  W  V  E  R  T  F  L  W   371

1120              1140              1160
1114 CTAGGCTATGCAAACTCTCTCATTAACCCTTTTATATATGCCTTCTTCAACCGGGACCTG 1173
372   L  G  Y  A  N  S  L  I  N  P  F  I  Y  A  F  F  N  R  D  L   391

1180              1200              1220
1174 AGGACCACCTATCGGAGCCTGCTCCAGTGCCAGTACCGGAATATCAACCGGAAGCTCTCA 1233
392   R  T  T  Y  R  S  L  L  Q  C  Q  Y  R  N  I  N  R  K  L  S   411
```

FIGURE 1-5

```
                    1240          1260          1280          1293
1234  GCTGCAGGCATGCATGAAGCCCTGAAGCTTGCTGAGAGGCCCAGAGAGACCTGAGTTTGTG
 412   A  A  G  M  H  E  A  L  K  L  A  E  R  P  E  R  P  E  F  V   431

1300          1320          1340          1353
1294  CTACAAAATGCTGACTACTGTAGAAAAAAGGTCATGATTGATTGAAAGCAGAACAA
 432   L  Q  N  A  D  Y  C  R  K  K  G  H  D  S  *                   445

1360
1354  TGGAGAGGAATTCGATATCAAGCTTA  1379
```

FIGURE 2-1

| | | | | | | |
|---|---|---|---|---|---|---|
| hp78a | MMDVNSSGRP | DLYGHLRSFL | LPEVGRGLPD | LSPDGGADPV | AGSWAPHLLS |
| 5HT$_{1A}$ | — | — | — | — | —MDVLS |
| 5HT$_{1D\alpha}$ | — | — | — | — | MSPLNQSAEG |
| 5HT$_{1D\beta}$ | — | — | —MEEPGAQC | — | APPPAGSET |
| 5HT$_{1E}$ | — | — | — | — | — |
| 5HT$_{1F}$ | — | — | — | — | — |

| | | | | | | |
|---|---|---|---|---|---|---|
| | | | | | I | |
| hp78a | EVTASPAPTW | DAPPDNASGC | GEQINYGRVE | KVVIGSILTL | ITLLTIAGNC |
| 5HT$_{1A}$ | PGQGNNTTSP | PAPFETGGNT | TGISDVTVSY | QVITSLLLGT | LIFCAVLGNA |
| 5HT$_{1D\alpha}$ | LPQEA---SN | RSLNATETSE | AWDPRTLQAL | KISLAVVLSV | ITLATVLSNA |
| 5HT$_{1D\beta}$ | WVPQANLSSA | PSQNCSAKDY | IYQDSISLPW | KVLLVMLLAL | ITLATTLSNA |
| 5HT$_{1E}$ | ------M | NITNCTTEAS | MAIRPKTITE | KMLICMTLVV | ITTLTLLNL |
| 5HT$_{1F}$ | — | — | ----MPS | KILVSLTLSG | LALMTTTINS |

FIGURE 2-2

```
                                              II
         ┌─────────────────────────────────────────────────────────────┐
hp78a    LVVISVCFVK  KLRQPSNYLI  VSLALADLSV  AVAVMPFVSV  TDLIGGKWIF
5HT1A    CVVAAIALER  SLQNVANYLI  GSLAVTDLMV  SVLVLPM-AA  LYQVLNKWTL
5HT1Dα   FVLTTILLTR  KLHTPANYLI  GSLATTDLLV  SILVMPI-SI  AYTITHTWNF
5HT1Dβ   FVIATVYRTR  KLHTPANYLI  ASLAVTDLLV  SILVMPI-ST  MYTVTGRWTL
5HT1E    AVIMAIGTTK  KLHQPANYLI  CSLAVTDLLV  AVLVMPL-SI  IYIVMDRWKL
5HT1F    LVIAAIIVTR  KLHHPANYLI  CSLAVTDFLV  AVLVMPF-SI  VYIVRESWIM

III
         ┌────────────────────────────────────────┐
hp78a    GHFFCNVFIA  MDVMCCTASI  MTLCVISIDR  YLGTTRPLTY  PVRQNGKCMA
5HT1A    GQVTCDLFIA  LDVLCCTSSI  LHLCAIALDR  YWAITDPIDY  VNKRTPRPRA
5HT1Dα   GQILCDIWLS  SDITCCTASI  LHLCVIALDR  YWAITDALEY  SKRRTAGHAA
5HT1Dβ   GQVVCDFWLS  SDITCCTASI  LHLCVIALDR  YWAITDAVEY  SAKRTPKRAA
5HT1E    GYFLCEVWLS  VDMTCCTCSI  LHLCVIALDR  YWAINAIEY   ARKRTAKRAA
5HT1F    GQVVCDIWLS  VDITCCTCSI  LHLSAIALDR  YRAITDAVEY  ARKRTPKHAG

IV
         ┌──────────────────────────┐
hp78a    KMILSVWLLS  ASITLPPLFG  W--AQNVNDD  KV-CLISQD-  FGYTIYSTAV
5HT1A    -LISLTWLIG  FLISIPPILG  WRTPEDRSDP  DA-CTISKDH  -GYTIYSTFG
5HT1Dα   TMIAIVWAIS  ICISIPPLF-  WRQAKAQEEM  SD-CLVNTSQ  ISYTIYSTCG
5HT1Dβ   VMIALVHVFS  ISISLPPFF-  WRQAKAEEEV  SE-CVVNTDH  ILYTVYSTVG
5HT1E    LMILTVWTIS  IFISMPPLF-  WRSHRRLSPP  PSQCTIQHDH  VIYTIYSTLG
5HT1F    IMITIVWIIS  VFISMPPLF-  WR-HQGTSRD  DE-CIIKHDH  IVSTIYSTFG
```

FIGURE 2-3

```
        -V-
hp78a    AFYIPMSVML FMYYQIYKAA RK-------- ---------- ---------- --SAAKHKFP
5HT_1A   AFYIPLLLML VLYGRIFRAA RFRIRKTVKK VEKTGADTRH GASPAPQPKK
5HT_1Dα  AFYIPSVLLI ILYGRIYRAA RNRIL----- ---------- ---------- -----NPPSL
5HT_1Dβ  AFYFPTLLLI ALYGRIYVEA RSRILK---- ---------- ---------- -----QTPNR
5HT_1E   AFYIPLTLIL ILYYRIYHAA KSLYQK---- ---------- ---------- -----RGSSR
5HT_1F   AFYIPLALIL ILYYKIYRAA KTLYHK---- ---------- ---------- -----RQASR hp78a    GFPRVEPDSV IALNGIVKLQ KEVEECANLS RLKKHERKNI SIF------- --------
5HT_1A   SVNGESGSRN WRLGVESKAG GALCANGAVR QGDDGAALEV IEVHRVGNSK
5HT_1Dα  -YGKRFTTAH LITGSAG--S SLCSLNSSLH EGHSH--SAGS PLEF------ --------
5HT_1Dβ  -TGKRLTRAQ LITDSPGSTS SVTSINSRVP DVPSE-S-GS PVYV------ --------
5HT_1E   HLSNRSTDSQ NSFA----SC KLTQTFCVSD FSTSDPTTEF EKFH------ --------
5HT_1F   -IAKEEVNGQ VLLESGEKST KSVSTSYVLE KSLSDPSTDF DKIH------ -------- hp78a    ---------- ---------- ---------- ----KREQK AATTLGIIVG
5HT_1A   EHLPLPSEAG PTPCAPASFE RKNERNAEAK RKMALARERK RKMALARERK TVKTLGIIMG
5HT_1Dα  ---NHV KIKLADSALE ----R----- KRISAARERK ATKILGIILG
5HT_1Dβ  ---NQV KVRVSDALLE ----K----- KKLMAARERK ATKTLGIILG
5HT_1E   -----ASI RIPPFDNDLD HPGER----- QQISSTRERK AARILGLILG
5HT_1F   -----STV RSLRSEFKHE KSWRR----- QKISGTRERK AATTLGLILG
```

FIGURE 2-4

```
                        VI                                                          VII
hp78a    AFTVCWLPFF  LLSTARPFIC  GTSCSCIPLW  VERTFLWLGY  ANSLINPFIY
5HT1A    TFILCWLPFF  IVALVLPF-C  ESSCH-MPTL  LGAIINWLGY  SNSLLNPVIY
5HT1Dα   AFIICWLPFF  VVSLVLP-IC  RDSCW-IHPA  LFDFFTWLGY  LNSLINPIIY
5HT1Dβ   AFIVCWLPFF  IISLVMP-IC  KDACW-FHLA  IFDFFTWLGY  LNSLINPIIY
5HT1E    AFILSWLPFF  IKELIVG-LS  --IYT-VSSE  VADFLTWLGY  VNSLINPLLY
5HT1F    AFVICWLPFF  VKELVVN-VC  -DKCK-ISEE  MSNFLAWLGY  LNSLINPLIY hp78a    AFFNRDLRTT  YRSLLQCQYR  NINRKLSAAG  MHEALKLAER  PERPEFVLQN
5HT1A    AYFNKDFQNA  FKKIIKCNFC  RQ*-------  ----------  ----------
5HT1Dα   TVFNEEFRQA  FQKIVPFRKA  S*--------  ----------  ----------
5HT1Dβ   TMSNEDFKQA  FHKLIRFKCT  S*--------  ----------  ----------
5HT1E    TSFNEDFKLA  FKKLIRCREH  T*--------  ----------  ----------
5HT1F    TIFNEDFKKA  FQKLVRCRC*  ----------  ----------  ---------- hp78a    ADYCRKKGHD  S*
5HT1A    ----------  --
5HT1Dα   ----------  --
5HT1Dβ   ----------  --
5HT1E    ----------  --
5HT1F    ----------  --
```

H2O

Frontal Brain

Total Brain

Kidney

Liver

Pancreas

Spleen

Heart Ventricle

Coronary Artery

Stomach

Descending Colon

Ileum

FIGURE 3

SEQUENCE LISTING

<160> NUMBER OF SEQ ID NOS: 12

<210> SEQ ID NO 1
<211> LENGTH: 1406
<212> TYPE: DNA
<213> ORGANISM: Homo sapiens
<220> FEATURE:
<221> NAME/KEY: CDS
<222> LOCATION: (28)..(1362)

<400> SEQUENCE: 1

| | | |
|---|---|---|
| ccatgggcag cggcacacgg cggcgcg atg atg gac gtt aac agc agc ggc cgc<br>                                              Met Met Asp Val Asn Ser Ser Gly Arg<br>                                                  1             5 | | 54 |
| ccg gac ctc tac ggg cac ctc cgc tct ttc ctt ctg cca gaa gtg ggg<br>Pro Asp Leu Tyr Gly His Leu Arg Ser Phe Leu Leu Pro Glu Val Gly<br> 10                      15                     20                   25 | | 102 |
| cgc ggg ctg ccc gac ttg agc ccc gac ggt ggc gcc gac ccg gtc gcg<br>Arg Gly Leu Pro Asp Leu Ser Pro Asp Gly Gly Ala Asp Pro Val Ala<br>                 30                          35                       40 | | 150 |
| ggc tcc tgg gcg ccg cac ctg ctg agc gag gtg aca gcc agc ccg gcg<br>Gly Ser Trp Ala Pro His Leu Leu Ser Glu Val Thr Ala Ser Pro Ala<br>                       45                       50                       55 | | 198 |
| ccc acc tgg gac gcg ccc ccg gac aat gcc tcc ggc tgt ggg gaa cag<br>Pro Thr Trp Asp Ala Pro Pro Asp Asn Ala Ser Gly Cys Gly Glu Gln<br>              60                          65                           70 | | 246 |
| atc aac tac ggc aga gtc gag aaa gtt gtg atc ggc tcc atc ctg acg<br>Ile Asn Tyr Gly Arg Val Glu Lys Val Val Ile Gly Ser Ile Leu Thr<br> 75                      80                     85 | | 294 |
| ctc atc acg ctg ctg acg atc gcg ggc aac tgc ctg gtg gtg atc tcc<br>Leu Ile Thr Leu Leu Thr Ile Ala Gly Asn Cys Leu Val Val Ile Ser<br> 90                      95                    100                105 | | 342 |
| gtg tgc ttc gtc aag aag ctc cgc cag ccc tcc aac tac ctg atc gtg<br>Val Cys Phe Val Lys Lys Leu Arg Gln Pro Ser Asn Tyr Leu Ile Val<br>                      110                    115                    120 | | 390 |
| tcc ctg gcg ctg gcc gac ctc tcg gtg gct gtg gcg gtc atg ccc ttc<br>Ser Leu Ala Leu Ala Asp Leu Ser Val Ala Val Ala Val Met Pro Phe<br>                  125                    130                    135 | | 438 |
| gtc agc gtc acc gac ctc atc ggg ggc aag tgg atc ttt gga cac ttt<br>Val Ser Val Thr Asp Leu Ile Gly Gly Lys Trp Ile Phe Gly His Phe<br>            140                    145                    150 | | 486 |
| ttc tgt aat gtc ttc atc gcc atg gac gtc atg tgc tgc acg gcc tcg<br>Phe Cys Asn Val Phe Ile Ala Met Asp Val Met Cys Cys Thr Ala Ser<br>155                     160                    165 | | 534 |
| atc atg acc ctg tgc gtg atc agc att gac agg tac ctt ggg atc aca<br>Ile Met Thr Leu Cys Val Ile Ser Ile Asp Arg Tyr Leu Gly Ile Thr<br>170                     175                    180                    185 | | 582 |
| agg ccc ctc aca tac cct gtg agg cag aat ggg aaa tgc atg gcg aag<br>Arg Pro Leu Thr Tyr Pro Val Arg Gln Asn Gly Lys Cys Met Ala Lys<br>                  190                    195                    200 | | 630 |
| atg att ctc tcc gtc tgg ctt ctc tcc gcc tcc atc acc tta cct cca<br>Met Ile Leu Ser Val Trp Leu Leu Ser Ala Ser Ile Thr Leu Pro Pro<br>            205                    210                    215 | | 678 |
| ctc ttt gga tgg gct cag aat gta aat gat gat aag gtg tgc ttg atc<br>Leu Phe Gly Trp Ala Gln Asn Val Asn Asp Asp Lys Val Cys Leu Ile<br>         220                    225                    230 | | 726 |
| agc cag gac ttt ggc tat acg att tac tct acc gca gtg gca ttt tat<br>Ser Gln Asp Phe Gly Tyr Thr Ile Tyr Ser Thr Ala Val Ala Phe Tyr<br>     235                    240                    245 | | 774 |

-continued

```
atc ccc atg tcc gtc atg ctt ttc atg tac tac cag att tac aag gct      822
Ile Pro Met Ser Val Met Leu Phe Met Tyr Tyr Gln Ile Tyr Lys Ala
250             255                 260                 265 gcc agg aag agt gct gcc aaa cac aag ttt cct ggc ttc cct cga gtg      870
Ala Arg Lys Ser Ala Ala Lys His Lys Phe Pro Gly Phe Pro Arg Val
                270                 275                 280 gag cca gac agc gtc atc gcc ctg aat ggc ata gtg aag ctc cag aag      918
Glu Pro Asp Ser Val Ile Ala Leu Asn Gly Ile Val Lys Leu Gln Lys
            285                 290                 295 gag gtg gaa gag tgt gca aac ctt tcg aga ctc ctc aag cat gaa agg      966
Glu Val Glu Glu Cys Ala Asn Leu Ser Arg Leu Leu Lys His Glu Arg
300                 305                 310 aaa aac atc tcc atc ttt aag cga gaa cag aaa gca gcc acc acc ctg     1014
Lys Asn Ile Ser Ile Phe Lys Arg Glu Gln Lys Ala Ala Thr Thr Leu
        315                 320                 325 ggg atc atc gtc ggg gcc ttt acc gtg tgc tgg ctg cca ttt ttc ctc     1062
Gly Ile Ile Val Gly Ala Phe Thr Val Cys Trp Leu Pro Phe Phe Leu
330                 335                 340                 345 ctc tcg aca gcc aga ccc ttc atc tgt ggc act tcc tgc agc tgc atc     1110
Leu Ser Thr Ala Arg Pro Phe Ile Cys Gly Thr Ser Cys Ser Cys Ile
                350                 355                 360 cca ctg tgg gtg gag agg aca ttt ctg tgg cta ggc tat gca aac tct     1158
Pro Leu Trp Val Glu Arg Thr Phe Leu Trp Leu Gly Tyr Ala Asn Ser
            365                 370                 375 ctc att aac cct ttt ata tat gcc ttc ttc aac cgg gac ctg agg acc     1206
Leu Ile Asn Pro Phe Ile Tyr Ala Phe Phe Asn Arg Asp Leu Arg Thr
380                 385                 390 acc tat cgc agc ctg ctc cag tgc cag tac cgg aat atc aac cgg aag     1254
Thr Tyr Arg Ser Leu Leu Gln Cys Gln Tyr Arg Asn Ile Asn Arg Lys
        395                 400                 405 ctc tca gct gca ggc atg cat gaa gcc ctg aag ctt gct gag agg cca     1302
Leu Ser Ala Ala Gly Met His Glu Ala Leu Lys Leu Ala Glu Arg Pro
410                 415                 420                 425 gag aga cct gag ttt gtg cta caa aat gct gac tac tgt aga aaa aaa     1350
Glu Arg Pro Glu Phe Val Leu Gln Asn Ala Asp Tyr Cys Arg Lys Lys
                430                 435                 440 ggt cat gat tca tgattgaaag cagaacaatg gagaggaatt cgatatcaag ctta    1406
Gly His Asp Ser
            445
```

<210> SEQ ID NO 2
<211> LENGTH: 445
<212> TYPE: PRT
<213> ORGANISM: Homo sapiens

<400> SEQUENCE: 2

```
Met Met Asp Val Asn Ser Ser Gly Arg Pro Asp Leu Tyr Gly His Leu
1               5                   10                  15

Arg Ser Phe Leu Leu Pro Glu Val Gly Arg Gly Leu Pro Asp Leu Ser
            20                  25                  30

Pro Asp Gly Gly Ala Asp Pro Val Ala Gly Ser Trp Ala Pro His Leu
        35                  40                  45

Leu Ser Glu Val Thr Ala Ser Pro Ala Pro Thr Trp Asp Ala Pro Pro
    50                  55                  60

Asp Asn Ala Ser Gly Cys Gly Glu Gln Ile Asn Tyr Gly Arg Val Glu
65                  70                  75                  80

Lys Val Val Ile Gly Ser Ile Leu Thr Leu Ile Thr Leu Leu Thr Ile
                85                  90                  95

Ala Gly Asn Cys Leu Val Val Ile Ser Val Cys Phe Val Lys Lys Leu
```

```
                    100                 105                 110
Arg Gln Pro Ser Asn Tyr Leu Ile Val Ser Leu Ala Leu Ala Asp Leu
        115                 120                 125
Ser Val Ala Val Ala Val Met Pro Phe Val Ser Val Thr Asp Leu Ile
130                 135                 140
Gly Gly Lys Trp Ile Phe Gly His Phe Cys Asn Val Phe Ile Ala
145                 150                 155                 160
Met Asp Val Met Cys Cys Thr Ala Ser Ile Met Thr Leu Cys Val Ile
                165                 170                 175
Ser Ile Asp Arg Tyr Leu Gly Ile Thr Arg Pro Leu Thr Tyr Pro Val
            180                 185                 190
Arg Gln Asn Gly Lys Cys Met Ala Lys Met Ile Leu Ser Val Trp Leu
        195                 200                 205
Leu Ser Ala Ser Ile Thr Leu Pro Pro Leu Phe Gly Trp Ala Gln Asn
    210                 215                 220
Val Asn Asp Asp Lys Val Cys Leu Ile Ser Gln Asp Phe Gly Tyr Thr
225                 230                 235                 240
Ile Tyr Ser Thr Ala Val Ala Phe Tyr Ile Pro Met Ser Val Met Leu
                245                 250                 255
Phe Met Tyr Tyr Gln Ile Tyr Lys Ala Ala Arg Lys Ser Ala Ala Lys
            260                 265                 270
His Lys Phe Pro Gly Phe Pro Arg Val Glu Pro Asp Ser Val Ile Ala
        275                 280                 285
Leu Asn Gly Ile Val Lys Leu Gln Lys Glu Val Glu Glu Cys Ala Asn
    290                 295                 300
Leu Ser Arg Leu Leu Lys His Glu Arg Lys Asn Ile Ser Ile Phe Lys
305                 310                 315                 320
Arg Glu Gln Lys Ala Ala Thr Thr Leu Gly Ile Ile Val Gly Ala Phe
                325                 330                 335
Thr Val Cys Trp Leu Pro Phe Phe Leu Leu Ser Thr Ala Arg Pro Phe
            340                 345                 350
Ile Cys Gly Thr Ser Cys Ser Cys Ile Pro Leu Trp Val Glu Arg Thr
        355                 360                 365
Phe Leu Trp Leu Gly Tyr Ala Asn Ser Leu Ile Asn Pro Phe Ile Tyr
    370                 375                 380
Ala Phe Phe Asn Arg Asp Leu Arg Thr Thr Tyr Arg Ser Leu Leu Gln
385                 390                 395                 400
Cys Gln Tyr Arg Asn Ile Asn Arg Lys Leu Ser Ala Ala Gly Met His
                405                 410                 415
Glu Ala Leu Lys Leu Ala Glu Arg Pro Glu Arg Pro Glu Phe Val Leu
            420                 425                 430
Gln Asn Ala Asp Tyr Cys Arg Lys Lys Gly His Asp Ser
        435                 440                 445
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 3
tgaccctgtg cgtgatcagc attg                                           24

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      primer/probe

<400> SEQUENCE: 4
gctttctgtt ctcgcttaaa gatggagatg                              30

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 5
cctgaatggc atagtgaagc tccagaagga ggtggaagag tgtgc             45

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 6
atgcttgagg agtctcgaaa ggtttgcaca ctcttccacc tcctt             45

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 7
agcattgaca ggtaccttgg gatcacaagg cccctcacat accct             45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 8
ccatgcattt cccattctgc ctcacagggt atgtgagggg ccttg             45

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 9
gtcagcgtca ccgacctcat cgggggcaag tggatctttg gacac             45

<210> SEQ ID NO 10

```
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 10
tggcgatgaa gacattacag aaaaagtgtc caaagatcca cttgc              45

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 11
ggcgccgacc cggtcgcggg ctcctgggca ccgcacctgc tgagc              45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 12
tgggcgccgg gctggctgtc acctcgctca gcaggtgcgg tgccc              45
```

DNA ENCODING A HUMAN SEROTONIN RECEPTOR (5-HT$_{4B}$) AND USES THEREOF

This application is a continuation of U.S. Ser. No. 09/332,837, filed Jun. 14, 1999, which is a continuation of U.S. Ser. No. 08/157,185, filed Jun. 15, 1995, now U.S. Pat. No. 5,985,585, issued Nov. 16, 1999, which was both a §371 national stage filing of PCT International Application No. PCT/US93/10553, filed Oct. 29, 1993, which claims priority of and was a continuation-in-part of U.S. Ser. No. 07/971,690, filed Nov. 3, 1992, now abandoned, and a continuation-in-part of U.S. Ser. No. 08/281,526, filed Jul. 27, 1994, now U.S. Pat. No. 6,083,749, issued Jul. 4, 2000.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

The subject invention of this application, DNA encoding a human serotonin receptor (5-HT$_{4B}$) and uses thereof, refers to the "5-HT$_{4B}$ receptor" which has been renamed to the "5-HT$_7$ receptor" by the "Serotonin Receptor Nomenclature Committee" of the IUPHAR. Thus, all claims herein directly or indirectly related to the 5-HT$_{4B}$ receptor and nucleic acid molecules encoding the 5-HT$_{4B}$ receptor are drawn to the 5-HT$_7$ receptor and nucleic acid molecules encoding the 5-HT$_7$ receptor also.

Primary amino acid sequence and signal transduction data are now published for four cloned 5-HT$_1$-like receptors, three cloned 5-HT$_2$ receptors, and one 5-HT$_3$ receptor. Analysis of the sequence homology as well as the signal transduction pathways of these receptors leads to their grouping on the basis of these attributes: The 5-HT$_1$ subfamily includes: 5-HT$_{1A}$ (Fargin, 1988; Kobilka, 1989), 5-HT$_{1B}$/5-HT$_{1D\beta}$(Weinshank et al., 1991 and the rest), 5-HT$_{1D\alpha}$, (Branchek et al. 1991; Hamblin and Metcalf, 1991; Weinshank et al., 1992), 5-HT$_{1E}$ (Levy et al., 1992; McAllister et al., 1992, Zgombick et al., 1992) and 5-HT$_{1F}$ (Adham et al, 1993). These subtypes share >50% transmembrane amino acid identity and couple to the inhibition of adenylate cyclase. The 5-HT$_2$ family includes the 5-HT$_2$ receptor (Pritchett et al., 1988), 5-HT$_{1C}$ (Julius et al., 1989) and 5-HT$_{2F}$ (Rat Stomach Fundus; Foquet et al., 1992; Kursar et al., 1992). These receptors share >70% amino acid identity and coupling to phosphoinositide hydrolysis. The 5-HT$_3$ receptor has been shown to be a ligand-gated ion channel (Maricq et al., 1991). Heterogeneity of 5-HT$_3$ receptors is controversial, although other ligand-gated ion channels display significant heterogeneity. Notably absent from this series are the 5-HT$_4$ receptors. The second messenger coupling from tissue studies indicates activation of adenylate cyclase as a primary mode of signal transduction (Dumius et al., 1988; Bockaert et al., 1990). We report here the cloning of the first mammalian 5-HT receptor that couples to the stimulation of adenylate cyclase activity which we propose to name 5-HT$_{4B}$. The pharmacological properties of this receptor indicate that it may be similar to a series of functionally defined 5-HT receptors described in the porcine vena cava (Trevethick et al., 1984), cat saphenous vein, coronary arteries [Cushing and Cohen, 1992, and several vascular dilatory effects (Mylecharane and Phillips, 1989). These receptors appear to underlie contractile and relaxant responses in isolated blood vessels indicating potential therapeutic benefit in angina, coronary artery disease, atherosclerosis, and possibly cerebral blood vessel disorders leading to stroke. The presence of this subtype in the CNS also indicates potential use in disorders of higher cognitive processes as well as control of autonomic function.

SUMMARY OF THE INVENTION

This invention provides an isolated nucleic acid molecule encoding a mammalian 5-HT$_{4B}$ receptor. In a preferred embodiment of this invention, the isolated nucleic acid encodes a human 5-HT$_{4B}$ receptor. In another embodiment of this invention, the nucleic acid molecule comprises a plasmid designated pcEXV-5-HT$_{4B}$ (ATCC Accession No. 75332).

This invention provides a nucleic acid probe comprising a nucleic acid molecule of at least 15 nucleotides capable of specifically hybridizing with a sequence included within the sequence of a nucleic acid molecule encoding a mammalian 5-HT$_{4B}$ receptor. This invention also provides a nucleic acid molecule of at least 15 nucleotides capable of specifically hybridizing with a sequence included within the sequence of a nucleic acid molecule encoding a human 5-HT$_{4B}$ receptor.

This invention provides an antisense oligonucleotide having a sequence capable of binding specifically to an mRNA molecule encoding a mammalian 5-HT$_{4B}$ receptor so as to prevent translation of the mRNA molecule. This invention also provides an antisense oligonucleotide having a sequence capable of binding specifically to an mRNA molecule encoding a human 5-HT$_{4B}$ receptor so as to prevent translation of the mRNA molecule.

This invention provides a monoclonal antibody directed to a mammalian 5-HT$_{4B}$ receptor. This invention also provides a monoclonal antibody directed to a human 5-HT4B receptor.

This invention provides a pharmaceutical composition comprising an amount of a substance effective to alleviate the abnormalities resulting from overexpression of a mammalian 5-HT$_{4B}$ receptor and a pharmaceutically acceptable carrier as well as a pharmaceutical composition comprising an amount of a substance effective to alleviate abnormalities resulting from underexpression of mammalian 5-HT$^{4B}$ receptor and a pharmaceutically acceptable carrier.

This invention provides a pharmaceutical composition comprising an amount of a substance effective to alleviate the abnormalities resulting from overexpression of a human 5-HT$_{4B}$ receptor and a pharmaceutically acceptable carrier. This invention also provides pharmaceutical composition comprising an amount of a substance effective to alleviate abnormalities resulting from underexpression of a human 5-HT$_{4B}$ receptor and a pharmaceutically acceptable carrier.

This invention provides a transgenic, nonhuman mammal whose genome comprises DNA encoding a mammalian 5-HT$_{4B}$ receptor so positioned within such genome as to be transcribed into antisense mRNA complementary to mRNA encoding the mammalian 5-HT$_{4B}$ receptor and when hybridized to mRNA encoding the mammalian 5-HT$_{4B}$ receptor, the complementary mRNA reduces the translation of the mRNA encoding the mammalian 5-HT$_{4B}$ receptor.

This invention also provides a transgenic, nonhuman mammal whose genome comprises DNA encoding a human 5-HT$_{4B}$ so positioned within such genome as to be transcribed into antisense mRNA complementary to mRNA encoding the human 5-HT$_{4B}$ and when hybridized to mRNA encoding the human 5-HT4B, the complementary mRNA reduces the translation of the mRNA encoding the human 5-HT$_{4B}$.

This invention provides a transgenic, nonhuman mammal whose genome comprises DNA encoding a mammalian 5-HT$_{4B}$ receptor positioned within such genome as to be transcribed into antisense mRNA which is complementary to mRNA encoding the mammalian 5-HT$_{4B}$ receptor and when hybridized to mRNA encoding the 5-HT$_{4B}$ receptor, the antisense mRNA thereby prevents the translation of mRNA encoding the 5-HT$_{4B}$ receptor.

This invention also provides a transgenic, nonhuman mammal whose genome comprises DNA encoding a human 5-HT4B receptor positioned within such genome as to be transcribed into antisense mRNA which is complementary to mRNA encoding the human 5-HT$_{4B}$ receptor and when hybridized to mRNA encoding human 5-HT$_{4B}$ receptor, the antisense mRNA thereby prevents the translation of mRNA encoding the 5-HT$_{4B}$ receptor.

This invention provides a method of screening drugs to identify drugs which specifically interact with, and bind to, a mammalian $^5$-HT$_{4B}$ receptor on the surface of a cell which comprises contacting a mammalian cell comprising an isolated DNA molecule encoding a mammalian 5-HT$_{4B}$ receptor, the protein encoded thereby is expressed on the cell surface, with a plurality of drugs, determining those drugs which bind to the mammalian cell, and thereby identifying drugs which specifically interact with, and bind to, a mammalian 5-HT$_{4B}$ receptor.

This invention provides a method of screening drugs to identify drugs which specifically interact with, and bind to, a human 5-HT$_{4B}$ receptor on the surface of a cell which comprises contacting a mammalian cell comprising an isolated DNA molecule encoding a human 5-HT$_{4B}$ receptor, the protein encoded thereby is expressed on the cell surface, with a plurality of drugs, determining those drugs which bind to the mammalian cell, and thereby identifying drugs which specifically interact with, and bind to, a human 5-HT$_{4B}$ receptor.

This invention also provides a method of determining the physiological effects of expressing varying levels of a mammalian 5-HT$_{4B}$ receptor which comprises producing a transgenic nonhuman animal whose levels of mammalian 5-HT$_{4B}$ receptor expression are varied by use of an inducible promoter which regulates mammalian 5-HT$_{4B}$ receptor expression.

This invention also provides a method of determining the physiological effects of expressing varying levels of a human 5-HT$_{4B}$ receptor which comprises producing a transgenic nonhuman animal whose levels of human 5-HT$_{4B}$ receptor expression are varied by use of an inducible promoter which regulates human 5 -HT$^{4B}$ receptor expression.

This invention further provides a method of determining the physiological effects of expressing varying levels of mammalian 5-HT$_{4B}$ receptor which comprises producing a panel of transgenic nonhuman animals each expressing a different amount of mammalian 5-HT$_{4B}$ receptor.

This invention further provides a method of determining the physiological effects of expressing varying levels of human 5-HT$_{4B}$ receptor which comprises producing a panel of transgenic nonhuman animals each expressing a different amount of human 5-HT$_{4B}$ receptor.

This invention provides a method for diagnosing a predisposition to a disorder associated with the expression of a human 5-HT$_{4B}$ receptor allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a 5-HT$_{4B}$ receptor and labelled with a detectable marker; e.) detecting labelled bands which have hybridized to the DNA encoding a 5-HT$_{4B}$ receptor labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for determining whether a substrate not known to be capable of binding to a can bind to a mammalian 5-HT$_{4B}$ receptor which comprises contacting a mammalian cell comprising an isolated DNA molecule encoding the mammalian 5-HT$_{4B}$ receptor with the substrate under conditions permitting binding of substrates known to bind to the 5-HT$_{4B}$ receptor, detecting the presence of any of the substrate bound to the 5-HT$_{4B}$ receptor, and thereby determining whether the substrate binds to the 5-HT$_{4B}$ receptor.

This invention provides a method for determining whether a substrate not known to be capable of binding to a human 5-HT$_{4B}$ receptor can bind to a human 5-HT$_{4B}$ receptor, which comprises contacting a mammalian cell comprising an isolated DNA molecule encoding the human 5-HT$_{4B}$ receptor with the substrate under conditions permitting binding of substrates known to bind to a human 5-HT$_{4B}$ receptor, detecting the presence of any of the substrate bound to the 5-HT$_{4B}$ receptor, and thereby determining whether the substrate binds to the human 5-HT$_{4B}$ receptor.

FIGURE LEGENDS

FIGS. 1-1–1-5. Nucleotide Sequence and Deduced Amino Acid Sequence of a Novel Human 5-HT$_{4B}$ Serotonin Receptor. Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionint (M), respectively.

FIGS. 2-1–2-4. Sequence Alignment of the Human 5-HT$_{4B}$ receptor clone (designated hp78a) with 5HT$_{1A}$, 5HT$_{1D\alpha}$, 5HT$_{1D\beta}$, 5HT$_{1E}$, and 5HT$_{1F}$. The deduced amino acid sequence of the human 5-HT$_{4B}$ receptor (first line), from the starting methionine (M) to the stop codon (*), is aligned with the human 5HT$_{1A}$ serotonin receptor clone (Kobilka et al., 1987), 5HT$_{1D\alpha}$serotonin receptor clone (Hamblin et al., 1991; Weinshank et al., 1992; Demchyshyn et al., 1992), 5HT$_{1D\beta}$serotonin receptor clone (Jin et al., 1992; Weinshank et al., 1992), 5HT$_{1E}$ serotonin receptor clone (Zgombick et al., 1992; McAllister et al., 1992), and 5HT$_{1F}$ serotonin receptor clone (Adham et al., submitted). Hyphens represent added spaces necessary for proper alignment. Gray shading indicates residues in receptor clones which are identical to the human 5-HT4B receptor. Numbers above amino acid sequences correspond to amino acid positions of the human 5-HT4B receptor, starting with the initiating methionine (M) and ending with the termination codon (*), and including spaces to account for proper alignment.

FIG. 3. Human tissue distribution of mRNA coding for 5HT$_{4B}$ receptor gene. Total RNA isolated from various human tissues were converted to single-stranded cDNA by random-priming with reverse transcriptase. cDNAs were amplified by PCR using functional hp78a-specific PCR primers. PCR products were run on a 1.5% agarose gel, blotted onto nylon membranes and hybridized to internal gene-specific oligonucleotides. Positive control consisted of gene-specific recombinant plasmid; dH$_2$O served as a negative control. PCR amplification and Southern blotting of RNA samples not treated with reverse transcriptase were negative.

FIG. 4. Stimulation of cAMP production by 5-HT in transiently transfected Cos-7 cells expressing the cloned human 5-HT$_{4B}$ receptor. cAMP measurements on intact cells were as described under Methods and Materials. Each data point represents the mean of triplicates from a single experiment representative of at least 2 others. The vertical bars indicate S.E.M. Data are presented as percent basal cAMP released (basal, 0.053±0.004 pmol/ml/10 min).

Figure 5:
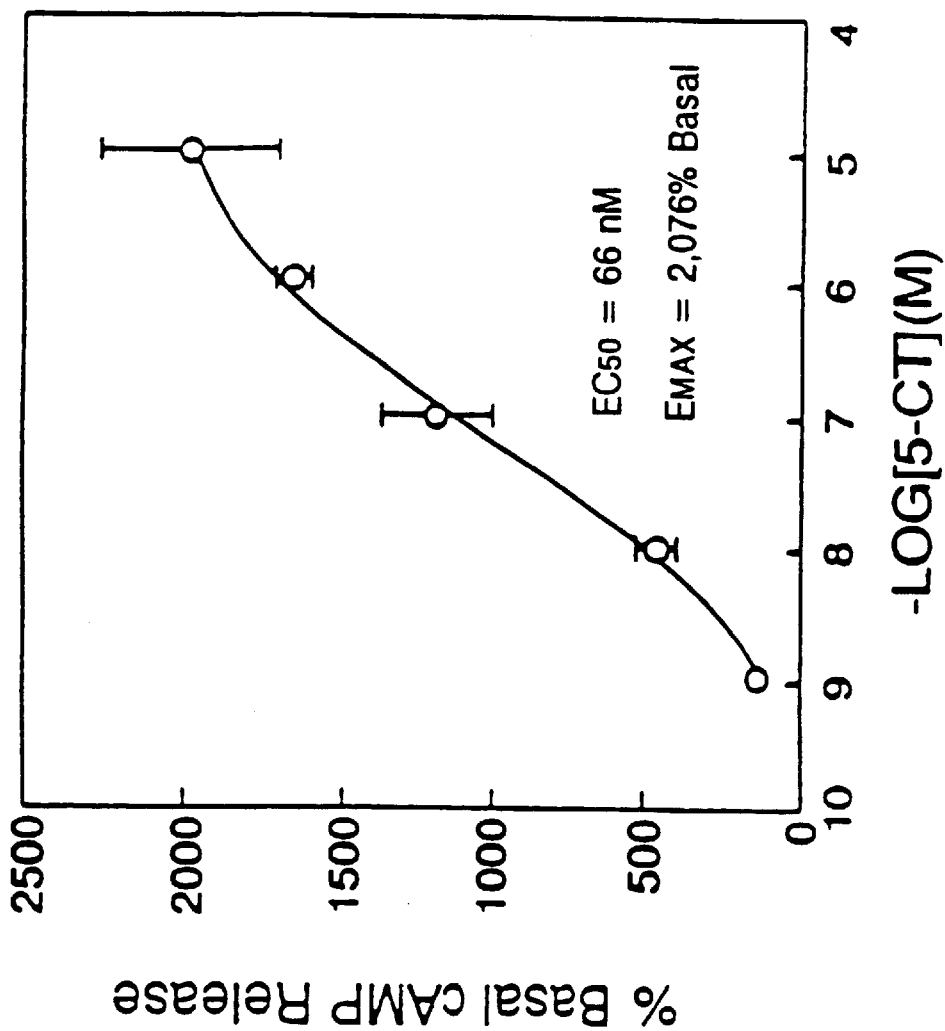

FIG. 5. Stimulation of cAMP production by 5-CT in transiently transfected Cos-7 cells expressing the cloned human 5-HT$_{4B}$ receptor. cAMP measurements on intact cells were as described under Methods and Materials. Each data point represents the mean of triplicates from a single experiment representative of at least 2 others. The vertical bars indicate S.E.M. Data are presented as percent basal cAMP released (basal, 0.053±0.004 pmol/ml/10 min).

DETAILED DESCRIPTION OF THE INVENTION

This invention provides an isolated nucleic acid molecule encoding a mammalian 5-HT$_{4B}$ receptor. This invention further provides an isolated nucleic acid molecule encoding a human 5-HT$_{4B}$ receptor. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or isolated genomic DNA molecule encoding a mammalian 5-HT$_{4B}$ receptor or a human 5-HT$_{4B}$ receptor. As used herein, "5-HT$_{4B}$ receptor" means a molecule which, under physiologic conditions, is substantially specific for the neurotransmitter serotonin, is saturable, of high affinity for serotonin and the activation of which is coupled to the activation of adenylate cyclase. One embodiment of this invention is an isolated nucleic acid molecule encoding a mammalian 5-HT$_{4B}$ receptor. Another, preferred embodiment is an isolated nucleic acid molecule encoding a human 5-HT$_{4B}$ receptor. Such a molecule may have coding sequences substantially the same as the coding sequences shown in FIGS. 1-1–1-5. The DNA molecule of FIGS. 1-1–1-5 (SEQ ID No: 1) encodes the sequence of a human 5-HT$_{4B}$ receptor. One means of isolating a mammalian 5-HT$_{4B}$ receptor is to probe a mammalian genomic library with a natural or artificially designed DNA probe, using methods well known in the art. In the preferred embodiment of this invention, the mammalian 5-HT$_{4B}$ receptor is a human protein and the nucleic acid molecule encoding the human 5-HT$_{4B}$ receptor is isolated from a human genomic library and human cDNA library, overlapping transmembrane oligonucleotide probes derived from the Drosophila serotonin receptor gene DRO5HTR are useful probes for this purpose. DNA and cDNA molecules which encode the human 5-HT$_{4B}$ receptor are used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5', untranslated region of the isolated clone, and other stability, processing, transcription, translation, and tissue specificity determining regions from the 3' and 5' untranslated regions of the isolated gene are thereby obtained.

This invention provides an isolated nucleic acid molecule which has been so mutated as to be incapable of encoding a molecule having normal 5-HT$_{4B}$ receptor activity, and not expressing native 5-HT$_{4B}$ receptor. An example of a mutated nucleic acid molecule provided by this invention is an isolated nucleic acid molecule which has an in-frame stop codon inserted into the coding sequence such that the transcribed RNA is not translated into protein.

This invention further provides a cDNA molecule encoding a mammalian 5-HT$_{4B}$ receptor, wherein the cDNA molecule has a coding sequence substantially the same as the coding sequence shown in FIGS. 1-1–1-5 (SEQ ID No: 1). This invention also provides a cDNA molecule encoding a human 5-HT$_{4B}$ receptor, wherein the cDNA molecule has a coding sequence substantially the same as the coding sequence shown in FIGS. 1-1–1-5. (Sequence I.D. No. 1). These molecules and their equivalents were obtained by the means described above.

This invention also provides an isolated protein which is a mammalian 5-HT$_{4B}$ receptor. In a preferred embodiment of this invention, the protein is a human 5-HT$_{4B}$ receptor protein having an amino acid sequence substantially similar to the amino acid sequence shown in FIGS. 1-1–1-5 (SEQ ID NO: 1). In another embodiment of this invention, the protein is a murine 5-HT$_{4B}$ receptor protein having an amino acid sequence substantially similar to the amino acid sequence shown in FIG. 1 (Seq. I.D. Nos. 1 and 2). As used herein, the term "isolated protein" is intended to encompass a protein molecule free of other cellular components. One means for obtaining an isolated mammalian $^5$-HT$_{4B}$ receptor protein is to express DNA encoding the 5-HT$_{4B}$ receptor in a suitable host, such as a bacterial, yeast, or mammalian cell, using methods well known to those skilled in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising an isolated nucleic acid molecule such as DNA, RNA, or cDNA, encoding a mammalian 5-HT$_{4B}$ receptor. This invention further provides a vector comprising an isolated nucleic acid molecule such as DNA, RNA, or cDNA, encoding a human 5-HT$_{4B}$ receptor. Examples of vectors are viruses such as bacteriophages (including but not limited to phage lambda), animal viruses (including but not limited to Baculovirus, Murine leukemia virus, and Herpes virus), cosmids, plasmids (such as pUC18, available from Pharmacia, Piscataway, N.J.), and other recombination vectors. Nucleic acid molecules are inserted into vector genomes by methods well known to those skilled in the art. Examples of such plasmids are plasmids comprising cDNA having a coding sequence substantially the same as the coding sequence shown in FIGS. 1-1–1-5 (SEQ ID NO: 1) and designated clone pcEXV-5HT$_{4B}$, deposited under ATCC Accession No. 75332.

Alternatively, to obtain these vectors, insert and vector DNA can both be exposed to a restriction enzyme to create complementary ends on both molecules which base pair with each other and are then ligated together with a ligase. Alternatively, linkers can be ligated to the, insert DNA which correspond to a restriction site in the vector DNA, which is then digested with the restriction enzyme which cuts at that site. Other means are also available.

This invention also provides vectors comprising a DNA molecule encoding a mammalian 5-HT$_{4B}$ receptor and vectors comprising a DNA molecule encoding a human 5-HT$_{4B}$ receptor, adapted for expression in a bacterial cell, a yeast cell, or a mammalian cell which additionally comprise the regulatory elements necessary for expression of the DNA in the bacterial, yeast, mammalian, or insect cells so located relative to the DNA encoding a mammalian 5-HT$_{4B}$ receptor or to the DNA encoding a human or mammalian 5-HT$_{4B}$ receptor as to permit expression thereof. DNA having coding sequences substantially the same as the coding sequence shown in FIG. 1 may be usefully inserted into these vectors to express a human 5-HT$_{4B}$ receptor. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Furthermore, an insect expression vector, such as recombinant Baculovirus, uses the polyhedrin gene expression signals for expression of the inserted gene in insect cells. Such vectors may be obtained commercially or assembled from the sequences described by methods well known in the art, for example the methods described above for constructing vectors in general. Expression vectors are useful to produce cells that express receptors. Certain uses for such cells are described in more detail below.

In one embodiment of this invention a plasmid is adapted for expression in a bacterial, yeast, insect or, in particular, a mammalian cell wherein the plasmid comprises a DNA molecule encoding a mammalian 5-HT$_{4B}$ receptor or a DNA molecule encoding a human 5-HT$_{4B}$ receptor and the regulatory elements necessary for expression of the DNA in the bacterial, yeast, insect or mammalian cell so located relative to the DNA encoding a mammalian 5-HT$_{4B}$ receptor or to the DNA encoding a human 5-HT$_{4B}$ receptor as to permit expression thereof. Suitable plasmids may include, but are not limited to plasmids adapted for expression in a mammalian cell, e.g., EVJB, EXV-3. An example of such a plasmid adapted for expression in a mammalian cell is a plasmid comprising cDNA having coding sequences substantially the same as the coding sequence shown in FIGS. 1-1-1-5 (SEQ ID No: 1) and the regulatory elements necessary for expression of the DNA in the mammalian cell. This plasmid has been designated pcEXV-5-HT$_{4B}$ deposited under ATCC Accession No. 75332. Those skilled in the art will readily appreciate that numerous plasmids adapted for expression in a mammalian cell which comprise DNA encoding a mammalian or human 5-HT$_{4B}$ receptor and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

Deposit discussed supra were made pursuant to, and in satisfaction of, the provisions of the Budapest Treaty on the International Recognition of the Deposit of Microorganisms for the Purpose of Patent Procedure with the American Type Culture Collection (ATCC), 10801 University Boulevard, Manassas, Va. 20110-2209, U.S.A.

This invention provides a mammalian cell comprising a DNA molecule encoding a mammalian 5-HT$_{4B}$ receptor, such as a mammalian cell comprising a plasmid adapted for expression in a mammalian cell, which comprises a DNA molecule encoding a mammalian 5-HT$_{4B}$ receptor and the regulatory elements necessary for expression of the DNA in the mammalian cell so located relative to the DNA encoding a mammalian 5-HT$_{4B}$ receptor as to permit expression thereof. This invention provides a mammalian cell comprising a DNA molecule encoding a human 5-HT$_{4B}$ receptor, such as a mammalian cell comprising a plasmid adapted for expression in a mammalian cell, which comprises a DNA molecule encoding a human $^5$-HT$_{4B}$ receptor and the regulatory elements necessary for expression of the DNA in the mammalian cell so located relative to the DNA encoding a human 5-HT$_{4B}$ receptor as to permit expression thereof. Numerous mammalian cells may be used as hosts, including, but not limited to, the mouse fibroblast cell NIH3T3, CHO cells, HeLa cells, LM (tk−) cells, Cos cells, etc. Expression plasmids such as that described supra may be used to transfect mammalian cells by methods well known in the art such as calcium phosphate precipitation, or DNA encoding a human or mammalian 5-HT$_{4B}$ receptor may be otherwise introduced into mammalian cells, e.g., by microinjection, to obtain mammalian cells which comprise DNA, e.g., cDNA or a plasmid, encoding a human or mammalian 5-HT$_{4B}$ receptor. LM (tk−) cells comprising and expressing the plasmid pcEXV-5HT$_{4B}$ were deposited with the ATCC as described hereinabove and given the ATCC Accession No. CRL 11166.

This invention provides a nucleic acid probe comprising a nucleic acid molecule of at least 15 nucleotides capable of specifically hybridizing with a sequence included within the sequence of a nucleic acid molecule encoding a human 5-HT$_{4B}$ receptor, for example with a coding sequence included within the sequences shown in FIGS. 1-1-1≡(SEQ ID NO: 1) As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding a human 5-HT$_{4B}$ receptor is useful as a diagnostic test for any disease process in which levels of expression of the 5-HT$_{4B}$ receptor are altered. DNA probe molecules are produced by insertion of a DNA molecule which encodes a 5-HT$_{4B}$ receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. An example of such DNA molecule is shown in FIG. 1. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encode a mammalian 5-HT$_{4B}$ receptor or complementary to the sequence of a DNA molecule which encodes a human 5-HT$_{4B}$ receptor are useful as probes for these genes, for their associated mRNA, or for the isolation of related genes by homology screening of genomic or cDNA libraries, or by the use of amplification techniques such as the Polymerase Chain Reaction.

This invention also provides a method of detecting expression of a human 5-HT$_{4B}$ receptor on the surface of a cell by detecting the presence of mRNA coding for a 5-HT$_{4B}$ receptor. This invention further provides a method of detecting expression of a mammalian 5-HT$_{4B}$ receptor on the surface of the cell by detecting the presence of mRNA coding for a mammalian 5-HT$_{4B}$ receptor. These methods comprise obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of the receptor by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (Maniatis, T. et al., Molecular Cloning; Cold Spring Harbor Laboratory, pp.197–98 (1982)). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mA molecule which encodes a human 5-HT$_{4B}$ receptor so as to prevent translation of the human 5-HT$_{4B}$ receptor. This invention also provides an antisense oligonucleotide having a sequence capable of binding specifically with any sequences of an mRNA molecule which encodes a mammalian 5-HT$_{4B}$ receptor so as to prevent translation of the mammalian 5-HT$_{4B}$ receptor. As used herein, the phrase "binding specifically" means the ability of an antisense oligonucleotide to recognize a nucleic acid sequence complementary to its own and to form double-helical segments through hydrogen bonding between complementary base pairs. The antisense oligonucleotide may have a sequence capable of binding specifically with any sequences of the cDNA molecule whose sequence is shown in FIG. 1. A particular example of an antisense oligonucleotide is an antisense oligonucleotide comprising chemical analogues of nucleotides.

This invention also provides a pharmaceutical composition comprising an effective amount of the oligonucleotide described above effective to reduce expression of a human 5-HT$_{4B}$ receptor by passing through a cell membrane and binding specifically with mRNA encoding the 5-HT$_{4B}$ receptor in the cell so as to prevent its translation and a pharmaceutically acceptable hydrophobic carrier capable of passing through a cell membrane. This invention further provides a pharmaceutical composition comprising an effective amount of the oligonucleotide described above effective to reduce expression of a mammalian 5-HT$_{4B}$ receptor by passing through a cell membrane and binding specifically with mRNA encoding a mammalian 5-HT$_{4B}$ receptor in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells. DNA molecules having a coding sequence substantially the same as the coding sequences shown in FIGS. 1-1–1-5 (SEQ ID. NO: 1) may be used as the oligonucleotides of the pharmaceutical composition.

This invention provides a method of treating abnormalities which are alleviated by reduction of expression of 5-HT$_{4B}$ receptor. This method comprises administering to a subject an effective amount of the pharmaceutical composition described above effective to reduce expression of the 5-HT$_{4B}$ receptor by the subject.

This invention further provides a method of treating an abnormal condition related to 5-HT$_{4B}$ receptor activity which comprises administering to a subject an amount of the pharmaceutical composition described above effective to reduce expression of the 5-HT$_{4B}$ receptor by the subject. Examples of such abnormal conditions are angina, coronary artery disease, atherosclerosis, cerebral blood vessel disorders leading to stroke, irritable bowel syndrome or other disorders of grastrointestinal motility, CNS disorders, pain perception, affective disorders, disorders of higher cognitive processes including but not limited to schizophrenia, as well as control of autonomic function.

Antisense oligonucleotide drugs inhibit translation of mRNA encoding 5-HT$_{4B}$ receptor. Synthetic antisense oligonucleotides, or other antisense chemical structures are designed to bind to mRNA encoding the 5-HT$_{4B}$ receptor and inhibit translation of mRNA and are useful as drugs to inhibit expression of 5-HT$_{4B}$ receptor genes in patients. This invention provides a means to therapeutically alter levels of expression of a human or mammalian $^5$-HT$_{4B}$ receptor by the use of a synthetic antisense oligonucleotide drug (SAOD) which inhibits translation of mRNA encoding the 5-HT$_{4B}$ receptor. Synthetic antisense oligonucleotides, or other antisense chemical structures designed to recognize and selectively bind to mRNA, are constructed to be complementary to portions of the nucleotide sequence shown in FIGS. 1-1-1-5 (SEQ ID NO: 1) of DNA, RNA or of chemically modified, artificial nucleic acids. The SAOD is designed to be stable ir. the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to transporter found only in a certain cell type, as discussed above. The SAOD is also designed to recognize and selectively bind to the target mRNA sequence, which may correspond to a sequence contained within the sequence shown in FIGS. 1-1–1-5 (SEQ ID NO: 1) by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10, 435 (1989); H. M. Weintraub, Sci. Am. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD servesas a therapy to reduce $5\text{-HT}_{4B}$ receptor expression in particular target cells of a patient, in any clinical condition which may benefit from reduced expression of $5\text{-HT}_{4B}$ receptor.

This invention provides an antibody directed to the human $5\text{-HT}_{4B}$ receptor. This invention also provides an antibody directed to the mammalian $5\text{-HT}_{4B}$ receptor. This antibody may comprise, for example, a monoclonal antibody directed to an epitope of a human $5\text{-HT}_{4B}$ receptor present on the surface of a cell, the epitope having an amino acid sequence substantially the same as an amino acid sequence for a cell surface epitope of the human $5\text{-HT}_{4B}$ receptor included in the amino acid sequence shown in FIGS. 1-1–1=(SEQ ID NO: 1). Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1-1–1=(SEQ ID NO: 1) will bind to a surface epitope of a $5\text{-HT}_{4B}$ receptor as described. Antibodies directed to a human or mammalian $5\text{-HT}_{4B}$ receptor may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or LM (tk⁻) cells may be used as immunogens to raise such an antibody. Alternatively, synthetic peptides may be prepared using commercially available machines and the amino acid sequences shown in FIGS. 1-1–1=(SEQ ID NO: 1). As a still further alternative, DNA, such as a cDNA or a fragment thereof, may be cloned and expressed and the resulting polypeptide recovered and used as an immunogen. These antibodies are useful to detect the presence of $5\text{-HT}_{4B}$ receptor encoded by the isolated DNA, or to inhibit the function of the $5\text{-HT}_{4B}$ receptor in living animals, in humans, or in biological tissues or fluids isolated from animals or humans.

This invention also provides a pharmaceutical composition which comprises an effective amount of an antibody directed to an epitope of the human or mammalian $5\text{-HT}_{4B}$ receptor, effective to block binding of naturally occurring substrates to the $5\text{-HT}_{4B}$ receptor, and a pharmaceutically acceptable carrier. A monoclonal antibody directed to an epitope of a human $5\text{-HT}_{4B}$ receptor present on the surface of a cell which has an amino acid sequence substantially the same as an amino acid sequence for a cell surface epitope of the human $5\text{-HT}_{4B}$ receptor included in the amino acid sequence shown in FIGS. 1-1–1-5 (SEQ ID NO: 1) is useful for this purpose.

This invention also provides a method of treating abnormalities in a subject which are alleviated by reduction of expression of a human or mammalian $5\text{-HT}_{4B}$ receptor which comprises administering to the subject an effective amount of the pharmaceutical composition described above effective to block binding of naturally occurring substrates to the receptor and thereby alleviate abnormalities resulting from overexpression of a human or mammalian $5\text{-HT}_4$ receptor. Binding of the antibody to the receptor prevents the receptor from functioning, thereby neutralizing the effects of overexpression. The monoclonal antibodies described above are useful for this purpose. This invention additionally provides a method of treating an abnormal condition related to an excess of $5\text{-HT}_{4B}$ receptor activity which comprises administering to a subject an amount of the pharmaceutical composition described above effective to block binding of naturally occurring substrates to the $5\text{-HT}_{4B}$ receptor and thereby alleviate the abnormal condition. Some examples of abnormal conditions associated with excess $5\text{-HT}_{4B}$ receptor activity are angina, coronary artery disease, atherosclerosis, cerebral blood vessel disorders leading to stroke, disorders of higher cognitive processes (e.g. schizophrenia) as well as control of autonomic function.

This invention provides methods of detecting the presence of a $5\text{-HT}_{4B}$ receptor on the surface of a cell which comprises contacting the cell with an antibody directed to the $5\text{-HT}_{4B}$ receptor, under conditions permitting binding of the antibody to the receptor, detecting the presence of the antibody bound to the cell, and thereby the presence of the $5\text{-HT}_{4B}$ receptor on the surface of the cell. Such methods are useful for determining whether a given cell is defective in expression of $5\text{-HT}_{4B}$ receptors. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a human $5\text{-HT}_{4B}$ receptor and a transgenic nonhuman mammal expressing DNA encoding a mammalian $5\text{-HT}_{4B}$ receptor. This invention also provides a transgenic nonhuman mammal expressing DNA encoding a human or mammalian $5\text{-HT}_{4B}$ receptor so mutated as to be incapable of normal receptor activity, and not expressing native 5-HT$_{4B}$ receptor. This invention further provides a transgenic nonhuman mammal whose genome comprises DNA encoding a human 5-HT$_{4B}$ receptor so placed as to be transcribed into antisense mRNA which is complementary to mRNA encoding a human 5-HT$_{4B}$ receptor which hybridizes to mRNA encoding a 5-HT$_{4B}$ receptor thereby reducing its translation and a transgenic nonhuman mammal whose genome comprises DNA encoding a mammalian 5-HT$_{4B}$ receptor so placed as to be transcribed into antisense mRNA which is complementary to mRNA encoding a mammalian 5-HT$_{4B}$ receptor and which hybridizes to mRNA encoding a mammalian 5-HT$_{4B}$ receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIGS. 1-1–1-5 (SEQ ID NO: 1). An example of a transgenic animal is a transgenic mouse. Examples of tissue specificity-determining regions are the metallothionein promotor (Low, M. J., Lechan, R. M., Hammer, R. E. et al. Science 231:1002–1004 (1986)) and the L7 promotor (Oberdick, J., Smeyne, R. J., Mann, J. R., Jackson, S. and Morgan, J. I. Science 248:223–226 (1990)).

Animal model systems which elucidate the physiological and behavioral roles of mammalian receptors are produced by creating transgenic animals in which the expression of a receptor is either increased or decreased, or the amino acid sequence of the expressed receptor protein is altered, by a variety of techniques. Examples of these techniques include, but are not limited to: 1) Insertion of normal or mutant versions of DNA encoding a human 5-HT$_{4B}$ receptor or homologous animal versions of this gene, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)) or, 2) Homologous recombination (Capecchi M. R. Science 244:1288–1292 (1989) ; Zimmer, A. and Gruss, P. Nature 338:150–153 (1989)) of mutant or normal, human or animal versions of these genes with the native gene locus in transgenic animals to alter the regulation of expression or the structure of the receptor. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a receptor is purified from a vector (such as plasmid pcEXV-5HT$_{4B}$ described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against the receptors even before such drugs become available. These animal model systems are useful for predicting or evaluating possible therapeutic applications of drugs which activate or inhibit receptors by inducing or inhibiting expression of the native or trans-gene and thus increasing or decreasing expression of normal or mutant receptors in the living animal. Thus, a model system is produced in which the biological activity of drugs directed against the receptors are evaluated before such drugs become available. The transgenic animals which over or under produce the receptor indicate by their physiological state whether over or under production of the receptor is therapeutically useful.

It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which down-regulates or acts as an antagonist to the receptor is indicated as worth developing, and if a promising therapeutic application is uncovered by these animal model systems, activation or inhibition of the 5-HT$_{4B}$ receptor is achieved therapeutically either by producing agonist or antagonist drugs directed against the 5-HT$_{4B}$ receptor or by any method which increases or decreases the expression of this receptor in man.

Further provided by this invention is a method of determining the physiological effects of expressing varying levels of human or mammalian 5-HT$_{4B}$ receptors which comprises producing a transgenic nonhuman animal whose levels of human or mammalian 5-HT$_{4B}$ receptor expression are varied by use of an inducible promoter which regulates receptor expression. This invention also provides a method of determining the physiological effects of expressing varying levels of human or mammalian 5-HT$_{4B}$ receptors which comprises producing a panel of transgenic nonhuman animals each expressing a different amount of human or mammalian 5-HT$_{4B}$ receptor. Such animals may be produced by introducing different amounts of DNA encoding a human or mammalian 5-HT$_{4B}$ receptor into the oocytes from which the transgenic animals are developed.

This invention also provides a method for identifying a substance capable of alleviating abnormalities resulting from overexpression of a human or mammalian 5-HT$_{4B}$ receptor comprising administering the substance to a transgenic nonhuman mammal expressing at least one artificially introduced DNA molecule encoding a human or mammalian 5-HT$_{4B}$ receptor and determining whether the substance alleviates the physical and behavioral abnormalities displayed by the transgenic nonhuman mammal as a result of overexpression of a human or mammalian 5-HT$_{4B}$ receptor. As used herein, the term "substance" means a compound or composition which may be natural, synthetic, or a product derived from screening. Examples of DNA molecules are DNA or cDNA molecules having a coding sequence substantially the same as the coding sequences shown in FIGS. 1-1-1≡(SEQ ID NO: 1).

This invention provides a pharmaceutical composition comprising an amount of the substance described supra effective to alleviate the abnormalities resulting from overexpression of 5-HT$_{4B}$ receptor and a pharmaceutically acceptable carrier.

This invention further provides a method for treating the abnormalities resulting from overexpression of a human or mammalian 5-HT$_{4B}$ receptor which comprises administering to a subject an amount of the pharmaceutical composition described above effective to alleviate the abnormalities resulting from overexpression of a human or mammalian 5-HT$_{4B}$ receptor.

This invention provides a method for identifying a substance capable of alleviating the abnormalities resulting from underexpression of a human or mammalian 5-HT$_{4B}$ receptor comprising administering the substance to the transgenic nonhuman mammal described above which expresses only nonfunctional human or mammalian 5-HT$_{4B}$ receptor and determining whether the substance alleviates the physical and behavioral abnormalities displayed by the transgenic nonhuman mammal as a result of unjerexpression of a human or mammalian 5-HT$_{4B}$ receptor.

This invention also provides a pharmaceutical composition comprising an amount of a substance effective to alleviate abnormalities resulting from underexpression of a human or mammalian 5-HT$_{4B}$ receptor and a pharmaceutically acceptable carrier.

This invention further provides a method for treating the abnormalities resulting from underexpression of a human or mammalian 5-HT$_{4B}$ receptor which comprises administering to a subject an amount of the pharmaceutical composition described above effective to alleviate the abnormalities resulting from underexpression of a human or mammalian 5-HT$_{4B}$ receptor.

This invention provides a method for diagnosing a predisposition to a disorder associated with the expression of a human or mammalian 5-HT$_{4B}$ receptor allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human or mammalian 5-HT$_{4B}$ receptor and labelled with a detectable marker; e) detecting labelled bands which have hybridized to the DNA encoding a the human or mammalian 5-HT$_{4B}$ receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific 5-HT$_{4B}$ human or mammalian 5-HT$_{4B}$ receptor allele.

This invention provides a method of preparing the isolated 5-HT$_{4B}$ receptor which comprises inducing cells to express receptor, recovering the receptor from the resulting cells, and purifying the receptor so recovered. An example of an 5-HT$_{4B}$ receptor is an isolated protein having substantially the same amino acid sequence as the amino acid sequence shown in FIGS. 1-1-1≡(SEQ ID NO: 1). For example, cells can be induced to express receptors by exposure to substances such as hormones. The cells can then be homogenized and the receptor isolated from the homogenate using an affinity column comprising, for example serotonin or another substance which is known to bind to the 5-HT$_{4B}$ receptor. The resulting fractions can then be purified by contacting them with an ion exchange column, and determining which fraction contains 5-HT$_{4B}$ receptor activity or binds anti-receptor antibodies.

This invention provides a method of preparing the isolated 5-HT$_{4B}$ receptor which comprises inserting nucleic acid encoding 5-HT$_{4B}$ receptor in a suitable vector, inserting the resulting vector in a suitable host cell, recovering the receptor produced by the resulting cell, and purifying the receptor so recovered. An example of an isolated $^5$-HT$_{4B}$ receptor is an isolated protein having substantially the same amino acid sequence as the amino acid sequence shown in FIGS. 1-1–1-5 (SEQ ID NO:1). These methods for preparing a-HT$_{4B}$ receptor uses recombinant DNA technology methods well known in the art. For example, isolated nucleic acid encoding 5-HT$_{4B}$ receptor is inserted in a suitable vector, such as an expression vector. A suitable host cell, such as a bacterial cell, or a eukaryotic cell such as a yeast cell, is transfected with the vector. 5-HT$_{4B}$ receptor is isolated from the culture medium by affinity purification or by chromatography or by other methods well known in the art.

This invention provides a method for determining whether a ligand not known to be capable of binding to a human 5-HT$_{4B}$ receptor can bind to a human 5-HT4B receptor which comprises contacting a mammalian cell comprising a DNA molecule encoding a human 5-HT$_{4B}$ receptor, the protein encoded thereby is expressed on the cell surface, with the ligand under conditions permitting binding of ligands known to bind to the 5-HT receptors, detecting the presence of any of the ligand bound to the 5-HT$_{4B}$ receptor, and thereby determining whether the ligand binds to the 5-HT$_{4B}$ receptor. This invention also provides a method for determining whether a ligand not known to be capable of binding to the human 5-HT$_{4B}$ receptor can functionally activate its activity or prevent the action of a ligand which does so. This comprises contacting a mammalian cell comprising an isolated DNA molecule which encodes a human 5-HT$_{4B}$ receptor with the ligand under conditions permitting the activation or blockade of a functional response, detected by means of a bioassay from the mammalian cell such as a second messenger response, and thereby determining whether the ligand activates or prevents the activation of the human 5-HT$_{4B}$ receptor functional output. The DNA in the cell may have a coding sequence substantially the same as the coding sequence shown in FIGS. 1-1–1-5 (SEQ ID NO: 1) preferably, the mammalian cell is nonneuronal in origin. An example of a nonneuronal mammalian cell is an Ltk- cell, in particular the Ltk- cell designated L-5-HT$_{4B}$. Another example of a non-neuronal mammalian cell to be used for functional assays is a murine fibroblast cell line, specifically the NIH3T3 cell. The preferred method for determining whether a ligand is capable of binding to the human 5-HT$_{4B}$ receptor comprises contacting a transfected nonneuronal mammalian cell (i.e. a cell that does not naturally express any type of 5-HT or G-protein coupled receptor, thus will only express such a receptor if it is transfected into the cell) expressing a 5-HT$_{4B}$ receptor on its surface, or contacting a membrane preparation derived from such a transfected cell, with the ligand under conditions which are known to prevail, and thus to be associated with, in vivo binding of the ligands to a 5-HT$_{4B}$ receptor, detecting the presence of any of the ligand being tested bound to the 5-HT$_{4B}$ receptor on the surface of the cell, and thereby determining whether the ligand binds to, activates or prevents the activation of the 5-HT$_{4B}$ receptor. This response system is obtained by transfection of isolated DNA into a suitable host cell containing the desired second messenger system such as phosphoinositide hydrolysis, adenylate cyclase, guanylate cyclase or ion channels. Such a host system is isolated from pre-existing cell lines, or can be generated by inserting appropriate components of second messenger systems into existing cell lines. Such a transfection system provides a complete response system for investigation or assay of the activity of human 5-HT$_{4B}$ receptor with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the human 5-HT$_{4B}$ receptor. The transfection system is also useful for determining the affinity and efficacy of known drugs at human 5-HT$_{4B}$ receptor sites.

This invention also provides a method of screening drugs to identify drugs which specifically interact with, and bind to, the human or mammalian 5-HT$_{4B}$ receptor on the surface of a cell which comprises contacting a mammalian cell comprising a DNA molecule encoding a human or mammalian 5-HT$_{4B}$ receptor on the surface of a cell with a plurality of drugs, detecting those drugs which bind to the mammalian cell, and thereby identifying drugs which specifically interact with, and bind to, the human and/or mammalian 5-HT$_{4B}$ receptor. Various methods of detection may be employed. The drugs may be "labeled" by association with a detectable marker substance (e.g., radiolabel or a non-isotopic label such as biotin). The DNA in the cell may have a coding sequence substantially the same as the coding sequence shown in FIGS. 1-1-1-5 (SEQ ID NO: 1). Preferably, the mammalian cell is nonneuronal in origin. An example of a nonneuronal mammalian cell is a Cos7 cell. Drug candidates are identified by choosing chemical compounds which bind with high affinity to the expressed 5-HT$_{4B}$ receptor protein in transfected cells, using radioligand binding methods well known in the art, examples of which are shown in the binding assays described herein. Drug candidates are also screened for selectivity by identifying compounds which bind with high affinity to one particular receptor but do not bind with high affinity to any other receptor subtypes or to any other known receptor. Because selective, high affinity compounds interact primarily with the target 5-HT$_{4B}$ receptor site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

Applicants have identified a novel human 5HT receptor subtype protein, designated 5-HT$_{4B}$ and have described methods for the identification of pharmacological compounds for therapeutic treatments. Pharmacological compounds which are directed against specific receptor subtypes provide effective new therapies with minimal side effects.

Elucidation of the molecular structures of the neuronal serotonin receptors is an important step in the understanding of serotonergic neurotransmission. This disclosure reports the isolation, amino acid sequence, and functional expression of a novel cDNA clone which encodes a human 5-HT$_{4B}$ receptor. The identification of 5-HT receptor subtypes play a pivotal role in elucidating the molecular mechanisms underlying serotonergic transmission, and should also aid in the development of novel therapeutic agents.

A complementary DNA clone (designated hp78a) encoding a serotonin receptor subtype has been isolated from human a human cDNA and genomic DNA library, and its functional properties have been examined in mammalian cells. The nucleotide sequence of predicts a protein of 445 amino acids with 7 highly hydrophobic regions compatible with membrane-spanning domains. Analysis of 5-HT$_{4B}$ structure and function provides a model for the development of drugs useful for the treatment of angina, coronary artery disease, atherosclerosis, cerebral blood vessel disorders leading to stroke, irritable bowel syndrome or other disorders of gastrointestinal motility, CNS disorders, pain perception, affective disorders, and disorders of higher cognitive processes including but not limited to schizophrenia, as well as control of autonomic function.

This invention identifies for the first time a mammalian serotonin receptor, its amino acid sequence, and its mammalian gene, the activation of which is information and experimental tools provided by this discovery are useful to generate new therapeutic agents, and new therapeutic or diagnostic assays for this receptor protein, its associated mRNA molecule or its associated genomic DNA. The information and experimental tools provided by this discovery will be useful to generate new therapeutic agents, and new therapeutic or diagnostic assays for this new serotonin receptor subtype, its associated mRNA molecule, or its associated genomic DNA.

Specifically, this invention relates to the isolation of mammalian cDNA and genomic DNA clones encoding a new serotonin receptor, designated 5-HT$_{4B}$. The new human gene for this receptor identified herein as hp78a has been identified and characterized and a series of related cDNA and genomic DNA clones have been isolated. In addition, the human 5-HT$_{4B}$ receptor has been expressed in Cos7 cells by transfecting the cells with the plasmid pcEXV-5HT$_{4B}$. The pharmacological binding properties of the encoded 5-HT$_{4B}$ receptor have been determined, and the binding properties classify this receptor as a novel serotonin receptor. Mammalian cell lines expressing the human 5-HT$_{4B}$ receptor on the cell surface has been constructed, thus establishing the first well-defined, cultured cell lines with which to study the novel 5-HT$_{4B}$ receptor.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Methods and Materials
Cloning and Sequencing

A human placenta genomic library in λ dash II (~1.5×10$^6$ total recombinants; Stratagene, Lajolla, Calif.) was screened using overlapping transmembrane (TM) oligonucleotide probes (TM 3, 5, 6 and 7) derived from the Drosophila serotonin receptor gene, Dro5HTR (Witz et al., 1990). Overlapping oligomers were labeled with [$^{32}$P]dATP and [$^{32}$P]dCTP by synthesis with the large fragment of DNA polymerase. Hybridization was performed at medium stringency conditions: 45° C. in a solution containing 37.5% formamide, 10% dextran sulfate, 5×SSC (1×SSC is 0.15M sodium chloride, 0.015M sodium citrate), 1×Denhardt's solution (0.02% polyvinylpyrrolindone, 0.02% Ficoll, 0.02% bovine serum albumin), and 200 μg/μl sonicated salmon sperm DNA. The filters were washed at 45° C. in 0.1×SSC containing 0.1% sodium dodecyl sulfate and exposed at −70° C. to Kodak XAR film in the presence of an intensifying screen. Lambda phage clones hybridizing with the probe were plaque purified and DNA was prepared for Southern blot analysis (Southern, 1975; Sambrook et al., 1989). For subcloning and further Southern blot analysis, DNA was cloned into pUC18 (Pharmacia, Piscataway, N.J.), pGEM-5Zf(Promega, Madison, Wis.) or pBluescriptII (Stratagene, LaJolla, Calif.). Nucleotide sequence analysis was accomplished by the Sanger dideoxy nucleotide chain termination method (Sanger et al., 1977) on denatured double-stranded plasmid templates, using Sequenase (US Biochemical Corp., Cleveland, Ohio), Bst DNA sequencing kit (Bio-Rad Laboratories, Richmond, Calif.), or TaqTrack sequencing kit (Promega Corporation, Madison, Wis.).

In order to isolate a full-length clone, human cDNA libraries were screened by polymerase chain reaction (PCR) with 1 μM each of specific oligonucleotide primers designed from the isolated genomic clone: from the sense strand (nucleotide 512–535), 5'TGACCCTGTGCGTGATCAG-CATTG 3' and from the anti-sense strand (nucleotide 945–974), 5 'GCTTTCTGTTCTCGCTTAAAGATG-GAGATG 3' (SEQ ID NO:4), (see FIG. 1). The primers were from the 3' end of Tm3 and the Tm5/Tm6 loop regions for the upstream and downstream primers, respectively. One to 2 μl of phage DNA from cDNA libraries (λ ZapII; Stratagene, LaJolla, Calif.), representing ≈10$^6$–10$^7$ pfu, were amplified in 10 mM Tris-HCl, pH 8.3, 50 mM KCl, 1.5 mM MgCl$_2$, 0.01% gelatin, 200 μM each DATP, dCTP, dGTP, dTTP, and 2.5 units of Thermus aquaticus DNA polymerase (Taq polymerase; Perkin-Elmer-Cetus, Norwalk, Conn.).

The amplification profile was run for 30 cycles: a 5 min. initial (ie. 1 cycle) denaturation at 95° C., followed by 2 min. at 94° C., 2 min. at 68° C., and 3 min. at 72° C., with a 3 sec. extension, followed by a final 10 min. extension at 72° C. PCR products were analyzed by ethidium bromide (EtBr) stained agarose gels and any sample exhibiting a band on the EtBr stained gel was considered positive.

A positive library was then plated and screened with overlapping 45-mer oligonucleotide probes, filled-in using [α-$^{32}$P]dCTP and (α-$^{32}$P]dATP and Klenow fragment of DNA polymerase. This probe was internal to the amplification primers discussed above: from the sense strand (nucleotide 864–908), 5'CCTGAATGGCATAGT-GAAGCTCCAGAAGGAGGTGGAAGAGTGTGC 3' (SEQ ID NO: 5), and from the antisense strand (nucleotide 889–933), 5'ATGCTTGAGGAGTCTCGAAAGGTTTG-CACACTCTTCCACCTCCTT 3 (SEQ ID NO: 6), (see FIGS. 1-1–1-5 (SEQ ID NO: 1). Positive cDNA phage clones were plaque purified and pBluescript recombinant DNAs were excision-rescued from λ Zap II using helper phage R408, as described by manufacturer's protocol (Stratagene, LaJolla, Calif.). Insert size was confirmed by restriction enzyme digest analysis and recombinants were sequenced, as described above.

Three additional sets of overlapping oligonucleotides were used to isolate a total of three partial but overlapping cDNA clones. These oligonucleotides and corresponding cDNA clone names are: from hFB9a (in the Tm3/4 loop), the sense strand (nt. 529–573), 5'AGCATTGACAGGTACCT-TGGGATCACAAGGCCCCTCACATACCCT 3' (SEQ ID NO: 7), and the antisense strand (nt. 554–599), 5'CCATG-CATTTCCCATTCTGCCTCACAGGGTAT-GTGAGGGGCCTTG 3' (SEQ ID NO: 8); from hFB44a (in Tm 2/3 loop), the sense strand (nt. 412–456), 5'GTCAGCGTCACCGACCT-CATCGGGGGCAAGTGGATCTTTGGACAC 3' (SEQ ID NO: 9), and the antisense strand (nt. 437–481), 5'TGGC-GATGAAGACATTACAGAAAAAGTGTC-CAAAGATCCACTTGC 3' (SEQ ID NO: 10); from hFB41a (in the NH$_2$ terminus), the sense strand (nt. 107–150) , 5'GGCGCCGACCCGGTCGCGGGCTC-CTGGGCACCGCACCTGCTGAGC 3' (SEQ ID NO: 11), and the antisense (nt. 131–175), 5'TGGGCGCCGGGCTG-GCTGTCACCTCGCTCAGCAGGTGCGGTGCCC 3' (SEQ ID NO: 12).

Expression

The entire coding region of the human 5-HT$_{4B}$ receptor (1338 bp), including 27 bp of 5' untranslated (5' UT) and 50 bp of 3' untranslated sequence (3' UT), was cloned into the SalI and EcoRI sites of the polylinker-modified eukaryotic expression vector pCEXV-3 (Miller et al, 1986), called EXJ.HR (unpublished data). The construct involved the ligation of three fragments from partial overlapping human placenta genomic and fetal brain cDNA clones: the start codon through TM 3 on a 0.5 kb NcoI-NcoI genomic fragment (the vector-derived SalI site was used for subcloning instead of the internal insert-derived NcoI site, at the 5' end), TM 3 alone synthesized as overlapping oligonucleotides (based on previously determined cDNA sequence) with NcoI and KpnI termini, and TM 3/4 loop through the stop codon and 3' UT, on a 0.8 kb KpnI-EcoRI cDNA fragment. Monkey kidney cells (Cos-7) were transiently transfected with plasmid hp78a/EXJ (expression vector encoding the human 5-HT$_{4B}$ receptor gene) using DEAE dextran methodology (reagents obtained from Specialty Media, Lavellette, N.J.). Cells were crown as monolayers in Dulbecco's modified Eagle medium (Gibco, Grand Island, N.Y.; 23) in a controlled environment (37° C., 5% $CO_2$). Stable cell lines were obtained by cotransfection with the plasmid hp78a/EXJ (expression vector containing the human 5-$HT_{4B}$ receptor gene) and the plasmid pGCcos3neo (plasmid containing the amino glycoside transferase gene) into LM (tk⁻) cells, using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin G, and 100 µg/ml streptomycin sulfate. Stable clones were then selected for resistance to the antibiotic G-418 (1 mg/ml) as described previously (Weinshank et al., 1990) and membranes were harvested and assayed for their ability to bind [$^3$H] hydroxytryptamine as described below (see Radioligand Binding Assays).

Macrolocalization (PCR/Tissue Transcriptional Expression Studies)

Human tissues (NDRI) were homogenized and total RNA extracted using guanidine isothiocyanate/CsCl cushion method as previously described (Kingston, 1987). cDNA was prepared from 5 µg of total RNA with random hexanucleotide primers (500 pmoles) using Superscript reverse transcriptase (BRL) in 50 mM Tris-HCl, pH 8.3, buffer containing 40 U RNasin, 2.5 mM $MgCl_2$, 50 mM KCl and 1 mM dNTPs, at 42° C. for 1 hr. RNase H (2 U) was added, incubated for 20 min. at 37° C., followed by heating at 95° C. for 5 min. and chilled on ice. An aliquot of the first strand cDNA was diluted (1:5) in a 50 µl PCR reaction mixture (200 µM dNTPs final concentration) containing 1.25 U of Taq polymerase in the buffer supplied by the manufacturer (Cetus Corp.), and 1 µM of primers in a PCR protocol (the 5' and 3' oligos were the same as used for screening cDNA libraries; see above). The PCR amplification reaction was carried out by first a 5 min. incubation at 95° C. followed by 30 rounds of the following cycle: 2 min. at 94° C., 2 min. at 68° C., 3 min. at 72° C., followed at the end by 10 min. incubation at 72° C. In order to control for the amplification of DNA (carried over during the RNA extraction), control PCR reactions were run in parallel with RNA diluted in the same manner as the cDNA sample. The PCR products were run on a 1.5% agarose gel and transferred to charged nylon membrane (ZetaProbe, Bio-Rad). Filters were hybridized with end-labeled (with [γ-$^{32}$P]ATP) internal probe to the PCR primers (this oligo was the same as used for screening the initial human fetal brain cDNA library; see above), washed under high stringency (50° C.), and exposed at −70° C. to Kodak XAR film in the presence of an intensifying screen, as described above.

Microlocalization (In Situ Hybridization)

Rats used for the in situ hybridization and receptor autoradiographic studies were euthanized with $CO_2$ and decapitated, and the brains dissected out and frozen in cold isopentane. The tissues were then mounted on cryostat chucks and sectioned serially at 11 µm for in situ hybridization, or at 20 µm for receptor autoradiography, in a cryostat maintained at −20° C. The sections were thaw-mounted on microscope slides coated with poly-l-lysine, air dried for one hour at room temperature, and stored at −80° C. until used.

Antisense and sense oligonucleotides (45 mers) to the rat 5-$HT_{4B}$ mRNA were synthesized on a Cyclone Plus DNA Synthesizer (Milligen/Biosearch). Probes were 3'-end labeled with $^{35}$S-dATP (1200 Ci/mmol, New England Nuclear, Boston, Mass.) to a specific activity of $10^9$ dpm/µg using terminal deoxynucleotidyl transferase (Boehringer Mannheim; Indianapolis, Ind.). The radiolabeled probes were purified on Biospin 6 chromatography columns (Bio-Rad: Richmond, Calif.), and diluted in hybridization buffer to a concentration of $1.5 \times 10^4$ cpm/µl. The hybridization buffer consisted of 50% formamide, 4×sodium citrate buffer (SSC; 1×=0.15 M NaCl and 0.015 M sodium citrate), 1×Denhardt's solution (0.2% polyvinylpyrrolidine, 0.2% Ficoll, 0.2% bovine serum albumin), 50 mM dithiothreitol, 0.5 mg/ml salmon sperm DNA, 0.5 mg/ml yeast tRNA, and 10% dextran sulfate.

Tissue sections were warmed to room temperature for 1 hr prior to use. The sections were fixed in 4% (w/v) paraformaldehyde in 10 mM phosphate-buffered saline (PBS), washed twice in PBS, rinsed with 5 mM DTT in water, acetylated for 10 min with 0.25% (v/v) acetic anhydride in 0.1 M triethanolamine, and rinsed twice in 2×SSC. The sections were then dehydrated in graded ethanols, delipidated with chloroform and air dried. One hundred µl of the diluted probe was applied to each section, which was then covered with a Parafilm coverslip. Hybridization was carried out overnight in humid chambers at 40 to 55° C. The following day the sections were washed in two changes of 2×SSC for one hour at room temperature, in 2×SSC for 30 min at 50–60° C., and finally in 0.1×SSC for 30 min at room temperature. Tissues were dehydrated in graded ethanols and apposed to Kodak XAR-5 film for 3 days to 2 weeks at −20° C., then dipped in Kodak NTB3 autoradiography emulsion diluted 1:1 with 0.2% glycerol water. After exposure at 4° C. for 2 to 4 weeks, the slides were developed in Kodak D-19 developer, fixed, and counterstained with hematoxylin and eosin.

Microlocalization (Receptor Autoradiography)

[$^3$H]5-CT binding was performed as follows. Mounted tissue sections (20 µm) were brought to room temperature, and preincubated for 15 min in buffer containing 0.17 M Tris-HCl, 4.0 mM $CaCl_2$, 0.01% (w/v) ascorbic acid, and 10 µM pargyline. The slides were incubated in 0.5 nM [$^3$H]5-carboxamidotyptamine (NEN, 50.4 Ci/mmol), for 1 hr at room temperature. To discriminate the 5-$HT_{4B}$ receptor from other serotonin receptors which also bind [$^3$H]5-CT, 100 nM PAPP and 160 nM (−)pindolol were used as masks. As the 5-$HT_{4B}$ receptor has a very high affinity for methiothepin, 5 nM methiothepin was added to the radioligand to eliminate [$^3$H]5-CT binding to the 5-$HT_{4B}$ receptor. Nonspecific binding was determined by adding 1 µM ergotamine to the radioligand. Following incubation in the radioligand, the slides were washed twice for 20 min in the above buffer at 4° C., rinsed briefly in ice-cold water, and dried under a gentle stream of warm air. The slides were apposed to Hyperfilm (Amersham) at room temperature for 4–6 weeks, after which the films were developed with D-19 (Kodak), fixed, and air dried.

Membrane Preparation

Cos-7 cells transiently transfected with the human 5-$HT_{4B}$ receptor gene were allowed to grow for 48 hrs. and membranes were harvested as previously described (Branchek et al., 1990). Membrane homogenates were kept on ice and utilized within one hr. for radioligand binding experiments. Protein concentrations were determined by the method of Bradford (Bradford, 1976) using bovine serum albumin as the standard.

Radioligand Binding Studies

Binding experiments were performed as previously described using [$^3$H]5-HT as the radioligand (Zgombick et al., 1991). Eight concentrations of [$^3$H]5-HT (1-100 nM) were used in saturation studies; seven concentrations of unlabelled compound and 5 nM [$^3$H]5-HT were used in competition experiments. Unlabeled 5-HT (10 µM) was used to define nonspecific binding. Assays were terminated by vacuum filtration (Brandel, Gaithersburg, Md.) and the remaining radioactivity was quantified using a Beckman 500TA liquid scintillation counter (Beckman Instruments, Fullerton Calif.)

Measurement of cAMP Formation

Transiently transfected Cos-7 cells expressing the human 5-HT$_{4B}$ receptor gene, mock-transfected Cos-7 cells, untransfected Cos-7 cells and stably transfected LM(tk−) cells were tested for the ability of 5-HT to modify intracellular cAMP levels. Both the 5-HT-mediated inhibition and stimulation of cAMP levels were evaluated in these three intact cell preparations. Intracellular cAMP formation was measured by radioimmunoassay (cAMP Radioimmunoassay kit, Advanced Magnetics, Cambridge, Mass.) using methodology outlined by Zgombick et al. (1991). Radioactivity was quantitatied using a Packard COBRA Auto Gamma Counter (equipped with data reduction software).

Data Analysis

Binding data was analyzed by nonlinear regression analysis (Accufit and Accucomp, Lundon Software, Chagrin Falls, Ohio). The Cheng-Prusoff equation was used to convert $IC_{50}$ values to $K_i$ values. Functional data was fitted to a four parameter logistic equation to obtain response parameters ($EC_{50}$, $E_{max}$, nH; Inplot, GraphPad, San Diego, Calif.). All experiments were performed a minimum of three times.

Drugs

Drugs were obtained from the following companies; [$^3$H]5-HT specific activity=20.4–28.0 Ci/mmole New England Nuclear, Boston, Mass.); 5-HT, ergotamine, ergonovine, oxymetazoline, (±)-pindolol, 5'-guanylylimidodiphosphate (Sigma, St. Louis, Mo.); 5-CT, DP-5-CT, 5-MeOT, 5-MeO-DMT, (±)-α-Me-5-HT, 2-Me-5-HT, tryptamine, DPAT, DOI, ketanserin, methysergide, 1-naphthylpiperazine, PAPP, spiperone, TFMPP, yohimbine, zacopride (Research Biochemical Inc, Natick, Mass.); lysergol, methylergonovine (Aldrich Chemicals, Milwaukee, Wis.) rauwolscine (Accurate Chemicals, Westbury, N.Y.); methiothepin (Biomol Research Laboratories, Plymouth Meeting, Pa.). All other chemicals were the highest purity available commercially.

Results

We screened a human genomic placenta library, under medium stringency conditions, with oligonucleotide probes directed to the third, fifth, sixth and seventh transmembrane regions of the Drosophila serotonin receptor gene, Dro5HTR (Witz et al, 1990). A total of 3 positive clones were isolated and characterized by Southern blot analysis. Two clones were identical and the other clone was an overlapping fragment of the other two. One of the two identical clones, designated hp78a, contained a 1.8 kb EcoRI/PstI fragment which hybridized with the Drosophila-derived oligonucleotide probes and was subsequently subcloned into a pUC vector. DNA sequence analysis indicated greatest homology to the Drosophila 5HT receptor, which is coupled to adenylate cyclase stimulation (Witz et al, 1990). Hydrophobicity plot of this subclone demonstrated regions of hydrophobic amino acid residues flanking segments of hydrophilic amino acid residues, consistent with it being a member of the seven transmembrane G-protein coupled receptor gene superfamily (Savarese et al., 1992). In addition, this clone contained an alanine residue in the predicted fifth transmembrane region, consistent with it being a member of the serotonin subfamily; this alanine residue distinguishes the serotonin subfamily from other catecholamine receptors (which have a serine residue at this position; Weinshank et al., 1992b). This clone encoded TM4 through the carboxyl terminus, including an intron upstream of the predicted second intracellular loop.

In order to obtain a full-length clone, aliquots of human cDNA libraries totaling ≈1.5×10$^6$ recombinants were screened by polymerase chain reaction using specific oligonucleotide probes from sequence determined off the genomic clone (see Materials and Methods). A positive-containing human fetal brain cDNA library (Stratagene, LaJolla, Calif.) in λ ZapII (≈1.5×10$^6$ recombinants) was screened using traditional plaque hybridization with an internal probe (see Materials and Methods) and resulted in the isolation of one positive partial-length cDNA clone, hFB9a, which contained TM3 through the stop codon and overlapped with the original genomic clone, hp78a (the intron between Tm3 and Tm4 was absent due to mRNA splicing). Because this cDNA clone was not full-length, the same human fetal brain cDNA library was screened with a probe derived from the most upstream non-conserved region of the hFB9a cDNA clone, corresponding to Tm3/4 loop (see Materials and Methods). This screen resulted in the isolation of another positive but partial-length cDNA clone, hFB44a, which contained only TM2 through TM3 and overlapped with the hFB9a cDNA clone within TM3. Again, to obtain 5' cDNA clones, the human fetal brain cDNA library was screened with a probe derived from the most upstream non-conserved region of the hFB44a cDNA clone, corresponding to TM2/3 loop (see Materials and Methods). This screen resulted in the isolation of another positive but partial-length cDNA clone, hFB41a, which contained part of the amino terminus through TM3, but missing about 20 amino acids from the start methionine residue (similarly, this clone overlapped with hFB44a cDNA clone in TM2 through TM3). Finally, to obtain the complete amino terminus, a human genomic placenta library was screened under high stringency with a probe derived from the non-conserved amino terminus region of the hFB41a cDNA clone. A total of 2 different positive clones were isolated from this genomic screen and were characterized by Southern blot analysis. One clone represented a pseudogene of the 5-HT$_{4B}$ receptor (unpublished data), whereas the other genomic clone contained the initiating methionine residue through the intron between TM3 and TM4. A 0.5 kb NcoI/NcoI fragment containing the initiating methionine to the NcoI site within TM3 was subcloned in pGEM.

The complete full-length gene was constructed in two parts: the first part involved ligating two fragments from two cDNA clones and a synthetic double-stranded oligonucleotide into pBluescript, and the second part involved ligating the amino terminus-containing genomic fragment and a fragment from the first part construct into an expression vector. The first part of the construction involved ligating a 0.4 kb SalI/NcoI fragment from hFB41a cDNA clone (SalI site is vector-derived, whereas the NcoI site is in Tm3), an annealed complementary double-stranded oligonucleotide fragment with designed NcoI and KpnI termini (≈100 bp; sequence based on data from the hFB9a, hFB44a, and hFB41a cDNA clones) and a 0.8 kb KpnI/EcoRI fragment from hFB9a cDNA clone (EcoRI is vector-derived, whereas the KpnI site is in TM3/4 loop) into pBluescript digested with SalI and EcoRI. The second part of the construction was perfromed by ligating the 0.5 kb SalI/NcoI genomic subclone, containing the initiating methionine through TM3 (SalI is vector-derived, whereas the NcoI is within TM3; this fragment was obtained by partial digestion with Nco I and complete digestion with SalI), with a 0.9 kb NcoI/EcoRI synthetic oligonucleotide/cDNA fragment from the first part construct (containing TM3 through the stop codon) into the expression vector digested with SalI and EcoRI.

The genomic/cDNA full-length construct in the expression vector (called hp78a/EXJ) contains an open reading frame of 1335 bp (with 27 bp at 5' UT and 50 bp at 3' UT) and encoding a protein of 445 aa in length, having a relative molecular mass of ≈49,000 daltons.

Hydropathy analysis of the protein is consistent with a putative topography of seven transmembrane domains, indicative of the G protein-coupled receptor family. Initial sequence analysis revealed that clone hp78a/EXJ was most related to a serotonin receptor since it contained a number of conserved structural features/residues found among the members of the serotonin receptor family, including conserved aspartic acid residues in TM2 and TM3, the Asp-Arg-Tyr sequence at the end of TM3, the conserved alanine residue in the fifth transmembrane region, and the conserved proline residues of Tm 4–7 (Hartig 1989; Hartig et al., 1990). Other features of this human $5-HT_{4B}$ receptor gene are the presence of two potential sites for N-linked glycosylation in the amino terminus (asparagine residues 5 and 66; FIGS. 1-1–1-5) and the presence of several serines and threonines in the carboxyl terminus and intracellular loops, which may serve as sites for potential phosphorylation by protein kinases.

Human Tissue Distribution of RNA Coding for $5-HT_{4B}$ Receptor Gene. Total RNA isolated from various human tissues were converted to single-stranded cDNA by random-priming with reverse transcriptase. cDNAs were amplified by PCR using human $5-HT_{4B}$ receptor gene specific PCR primers. PCR products were run on a 1.5% agarose gel, blotted onto nylon membranes and hybridized to internal gene-specific oligonucleotides. Following hybridization, blots were washed under high stringency. Positive control consisted of gene-specific recombinant plasmid; $dH_{20}$ served as a negative control, containing all reagents except template cDNA, RNA or plasmid. PCR amplification and Southern blotting of RNA samples not treated with reverse transcriptase were negative.

TABLE 1

Human tissue localization of $5-HT_{4B}$ receptor mRNA

| HUMAN TISSUES | $5-HT_{4B}$ mRNA |
|---|---|
| Prostate III | + |
| Prostate IV | + |
| Prostate V | +½ |
| Testes | +++ |
| Bladder | +++ |
| Endometrium (uterus) | ½+ |
| Myometrium (uterus) | ½+ |
| Atrium | ½+ |
| Mesentery | + |
| Nasal Mucosa | ++ |
| Penis | ++ |
| Skin | (−) |
| Tongue | (−) |

+++ = dark
++ = moderate
+ = present but faint
− = absent

The expression of hp78a transcripts was analyzed by amplification of cDNA derived from RNA isolated from various human tissues (reverse transcription PCR or RT-PCR) (FIG. 3). We were able to examine, selectively, the tissue distribution of the functional hp78a clone (and not the pseudogene) by using gene-specific PCR primers and gene-specific internal oligonucleotide probes, which failed to detect the pseudogene (data not shown). We demonstrated comparable quantities of starting RNA for all tissues by conducting control RT-PCR with primers for the moderately high level constituitively expressed genes, actin and glyceraldehyde 3-phosphate dehydrogenase (Clontech; data not shown). The mRNA encoding the $5-HT_{4B}$ receptor (hp78a) receptor is expressed at high levels in the brain and at low levels in a variety of peripheral tissues (kidney, liver, pancreas, prostate, uterus, mesentary and spleen). Based on the pharmacological profile of the $5-HT_{4B}$ receptor and its relationship to the previously characterized 5-HT receptors which mediate smooth muscle relaxation, we tested a number of additional tissues for RNA expression. Interestingly, we detected high levels of mRNA for $5-HT_{4B}$ in the coronary artery and in various regions of the gastrointestinal tract, including the stomach, bladder, descending colon and ileum, consistent with the possible role of $5-HT_{4B}$ as a smooth muscle relaxant receptor (FIG. 3).

The results of the in situ hybridization studies (Table 2) indicated that the distribution of the $5-HT_{4B}$ mRNA overlapped that of the $5-HT_{4B}$ receptor in some areas. The most intense hybridization signals were observed over neurons in the thalamus, the anterior hippocampal rudiment, and over CA3 in the hippocampus. Other regions containing hybridization signals included the septum, the hypothalamus, the centromedial amygdala, and the periaquaductal gray. Interestingly, two areas which exhibited a robust receptor binding signal, the globus pallidus and the substantia nigra, contained no $5-HT_{4B}$ hybridization signals, suggesting a presynaptic localization for $5-HT_{4B}$ receptors in these two related structures.

Specific binding of $[^3H]$5-CT was observed in many areas of the rat brain. Following incubation with 1 μM ergotamine, this binding was completely eliminated. Addition of PAPP and (−)pindolol to the radioligand markedly reduced the binding in a number of regions, most notably in the deep layers of the cerebral cortex, hippocampus, dorsal raphe, and spinal cord. Areas in which $[^3H]$5-CT binding remained following addition of the masks were layers 1–3 of cortex, septum, globus pallidus, thalamus, hypothalamus, centromedial amygdala, substantia nigra, periaquaductal gray, and superior colliculus. The radioligand binding in all of these areas was abolished by the addition of 5 μM methiothepin to the incubation regimen, indicating that the observed binding was attributable to $5-HT_{4B}$ receptors.

TABLE 2

Localization of the $5HT_{4B}$ Receptor/mRNA in Rat Brain

| REGION | $[^3H]$ 5-CT Binding Sites | $5-HT_{4B}$ mRNA |
|---|---|---|
| Cerebral cortex layers I, II and III | + | + |
| Septum | + | + |
| Globus pallidus | + | − |
| Bed n. stria terminalis | + | + |
| Thalamic nuclei | + | + |
| Hypothalamic n. | + | + |
| Amygdala (centromedial complex) | + | + |
| Hippocampus[A] | + | + |
| Central gray | + | + |
| Substantia nigra | + | − |
| Superior colliculus | + | ± |

TABLE 2-continued

Localization of the 5HT$_{4B}$ Receptor/mRNA in Rat Brain

| REGION | [$^3$H] 5-CT Binding Sites | 5-HT$_{4B}$ mRNA |
|---|---|---|
| Dorsal cortex Inferior Colliculus | + | nd |
| Cerebellum | − | + |

$^A$Very low number of binding sites by receptor autoradiography, however, by in situ hybridization moderate levels of 5-HT$_{4B}$ mRNA transcripts were detected: CA3 > DG > CA1.
nd = not done Monkey kidney cells transiently expressing the gene encoding the novel human 5-HT receptor were used for pharmacological evaluation. Membranes harvested from transiently transfected Cos-7 cells exhibited high affinity, saturable [$^3$H]5-HT binding. Nonlinear analysis of [$^3$H]5-HT saturation data yielded an equilibrium dissociation constant ($K_d$) of 8.5±0.8 nM and a binding site density ($B_{max}$) of 6.6±0.8 pmol/mg protein. Specific [$^3$H]5-HT binding was greater than 90% of total binding at a radioligand concentration equal to the $K_d$ value. High affinity [$^3$H]5-HT binding to membranes prepared from transient transfectants was reduced significantly (75%) by 100 μM Gpp(NH)p, a non-hydrolyzable analog of GTP. Untransfected host cells did not displayed specific [$^3$H]5-HT binding.

To further assess the pharmacological identity of the newly isolated serotonin receptor gene, detailed binding properties of clone hp78a were determined from nonlinear analysis of competition of high affinity [$^3$H]5-HT binding. Specific [$^3$H]5-HT binding was completely displaced in a monophasic manner ($n_H$=1) by a variety of structurally diverse serotonergic ligands. The rank order of potency of these compounds to displace specific [$^3$H]5-HT binding was 5-CT>methiothepin>Metergoline=DHE=5-MeOT>5-HT>2-Br-LSD>DP-5-CT>DPAT>sumatriptan>ICS 203930 (Tables 3 and 4). Several ergot derivatives exhibited high affinity ($K_i$<20 nM) for clone 5-HT$_{4B}$ receptor and include metergoline, dihydroergotamine, ergotamine, and mesulergine. Serotonergic ligands which display subtype selectivity and which exhibit low affinity ($K_i$>100 nM) for the clone hp78a include DPAT (5-HT$_{1A}$), sumatriptan (5-HT$_{1D}$), ketanserin (5-HT$_2$), and zacopride (5-HT$_3$). The substituted benzamides (ICS 203930, MDL 29429, zacopride), compounds which are active at the functional 5-HT$_4$ receptor, also displayed low affinity ($K_i$>500 nM) for the 5HT$_{4B}$ receptor. Other biogenic amines did not show appreciable affinity ($K_i$>1 μM) for clone hp78a (Tables 3 and 4).

TABLE 3

| COMPOUND | K$_i$ (nM) |
|---|---|
| 5-Carboxamidotryptamine | 0.93 ± 0.20 |
| Methiothepin | 3.7 ± 1.0 |
| 5-Methoxytryptamine | 5.1 ± 0.4 |
| Metergoline | 6.4 ± 1.4 |
| Dihydroergotamine | 6.9 ± 0.9 |
| 5-Hydroxytryptamine | 8.1 ± 1.3 |
| Ergotamine | 15 |
| Mesulergine | 18 ± 5 |

TABLE 3-continued

| COMPOUND | K$_i$ (nM) |
|---|---|
| Bufotenin | 26 |
| 2-Bromo-LSD | 30 ± 10 |
| Dipropyl-5-carboxamidotryptamine | 37 ± 21 |
| 5-Methoxy-N,N-dimethyltryptamine | 43 |
| Ritanserin | 45 ± 10 |
| Clozapine | 78 ± 10 |
| Methysergide | 83 ± 5 |
| 1-Naphthylpiperazine | 83 ± 19 |
| Spiperone | 110 ± 17 |
| Cyproheptadine | 123 ± 16 |
| Bromocriptine | 137 ± 2 |
| Tryptamine | 149 ± 20 |
| m-Chlorophenylpiperazine | 312 |
| 8-Hydroxy-N,N-dipropylaminotetralin | 466 ± 46 |
| α-Methyl-5-hydroxytryptamine | 509 |
| 5-Benzyloxytryptamine | 729 |
| Sumatriptan | 951 ± 118 |
| Ketanserin | 1334 ± 241 |
| Yohimbine | 2850 ± 354 |
| 2-Methyl-5-hydroxytryptamine | 3400 |
| Pindolol | >5000 |
| Zacopride | >5000 |

Apparent dissociation constants ($K_i$ values) of serotonergic ligands for clone hp78a. Membranes were incubated with 5 nM [$^3$H] 5-HT in the presence of seven concentrations (1000-fold concentration range) of unlabelled competitors for 30 min at 37° C. Nonspecific binding was defined by 10 μM unlabelled 5-HT. Affinity constants ($K_i$ values) were calculated from IC$_{50}$ values by nonlinear regressionanalysis using the Cheng-Prusoff equation. K$_i$ values are exp

TABLE 4

| COMPOUND | CONCENTRATION TESTED | PERCENT INHIBITION |
|---|---|---|
| d-LSD | 30 nM | 77 |
| BRL 29429 | 100 nM | 8 |
| ICS 203930 | 1000 nM | 10 |
| Spiroxatrine | 30 nM | 12 |
| Propranolol | 100 nM | 0 |
| PAPP | 100 nM | 21 |
| CGS 12660B | 100 nM | 15 |
| Quipazine | 100 nM | 3 |
| Rauwolscine | 100 nM | 8 |
| DOI | 100 nM | 20 |
| Oxymetazoline | 10 nM | 6 |
| Dopamine | 30 nM | 0 |
| Norepinephrine | 30 nM | 0 |
| Histamine | 100 nM | 10 |

Percent displacement of specific [$^3$H] 5-HT binding to membranes derived from cells transiently expressing the hp78a gene by serotonergic ligands. Membranes were incubated with 5 nM [$^3$H] 5-HT and one concentration of unlabelled competitor for 30 min at 37° C. Nonspecific binding was defined by 10 μM unlabelled 5-HT.

The ability of clone hp78a to functionally couple to adenylate cyclase was tested using intact Cos-7 cells transiently expressing the gene encoding hp78a. Both the stimulation of basal cAMP release and inhibition of FSK-stimulated cAMP response were investigated. 5-HT (1 μM) had no effect on either basal or FSK-stimulated adenylate cyclase activity in untransfected or mock-transfected Cos-7 cells (data not shown), indicating that endogenous cyclase-coupled serotonin receptors are not expressed in untransfected cells. Addition of 5-HT (1 μM) to transfected Cos-7 cells elicited a 7-fold stimulation of basal cAMP release (0.035±0.004 pmol/ml/10 min); inhibition of either the basal or FSK-stimulated cAMP release was not observed. Coincubation of 1 μM FSK and 1 μM 5-HT evoked a synergistic cAMP response, resulting in a 75-fold stimulation of intracellular cAMP accumulation (data not shown). 5-CT and 5-MeOT were also potent agonists at 1 μM, interestingly 5-CT appeared to be more potent than 5-HT itself, whereas 8-OH-DPAT stimulated the basal cAMP response by only about 2 fold at 1 μM. Methysergide, metergoline and methiothepin at 10 μM, antagonized the 5-HT response almost completely, whereas ICS-205-930 had a weak inhibitory effect at 100 μM. Full dose-response curves were determined for 5-HT and 5-CT. 5-HT exhibited an $EC_{50}$ value of 992±345 nM and a maximum stimulation ($E_{max}$ value) of 2,191±715% basal cAMP release (n=4) whereas 5-CT had a higher affinity ($EC_{50}$=75±15 nM) with a similar $E_{max}$ (2029±47% basal cAMP release, n=4) (Table 5; FIGS. 4 and 5).

release was not observed. The affinity values of various compounds tested are summarized in Table 6. In general the $EC_{50}$ values of agonists obtained from functional studies were about one order of magnitude lower than the $K_i$ values obtained from the binding assays. 5-CT and 5-MeOT were potent agonists having comparable intrinsic activity to 5-HT, however 5-CT had significantly greater affinity (approximately 10-fold) than 5-HT. 8-OH-DPAT was a weak agonist producing approximately half of the maximum response elicited by 5-HT. All the ergot alkaloids tested

TABLE 5

Pharmacological profile for the cAMP response using the human 5-$HT_{4B}$ receptor transiently expressed in Cos-7 cells. cAMP measurements on intact cells were as described under Methods and Materials. Drug activity was measured in triplicate at the single indicated. Results for agonists are expressed as fold cAMP stimulation relative to basal levels (basal, 0.053 ± pmol/ml/10 min). Data for antagonists are expressed as % inhibition of the cAMP response to 1 μM 5-HT.

| STRUCTURAL CLASS | DRUG | [DRUG] | FOLD cAMP STIMULATION | % INHIBITION OF 5-HT RESPONSE |
|---|---|---|---|---|
| INDOLEAMINES | 5-HT | 1 μM | 6.7 ± 0.65 | |
| | 5-CT | 1 μM | 28 ± 5.5 | |
| | 5-MeOT | 1 μM | 6.0 ± 0.08 | |
| | ICS-205-930 | 100 μM | 0 | 36 ± 3.0 |
| ERGOLINES | Methysergide | 10 μM | 1.7 ± 0.43 | 82 ± 1.5 |
| | Metergoline | 10 μM | 0 | 96 ± 1.0 |
| PIPERAZINES | Methiothepin | 10 μM | 0 | 100 ± 0 |
| | 2,Bromo LSD | 1 μM | 0 | 95 ± 4.5 |
| BENZAMIDES | BRL 29429 | 10 μM | 0 | |
| AMINOTETRALIN | DPAT | 1 μM | 1.7 ± 0.4 | |

In stably transfected LM (tk⁻) cells 5-HT produced a maximum stimulation of 400% of basal cAMP accumulation. Inhibition of either the basal or FSK-stimulated cAMP release was not observed. behaved as silent antagonists with $K_B$ values not deviating significantly from $K_i$ values obtained from binding assays.

Methiothepin was also a potent silent antagonist (Table 6).

TABLE 6

Pharmacological profile for the cAMP response using the human 5-$HT_{4B}$ receptor stably expressed in LM (tk–) cells. cAMP measurements on intact cells were as described under Methods and Materials. Average maximum response to 5-HT in these cells is 400% stimulation of basal cAMP production. $E_{max}$ values are normalized to the 5-HT maximal response. AGONIST indicates that the maximal response to the drug was at least 80% of the maximum response obtained with 5-HT (400% stimulation of basal cAMP accumulation). Results are means ± S.E.M. of at least 3 experiments performed in triplicate. Dissociation constant of antagonist ($K_B$) was calculated According to the formula: $K_B = [B]/(A'/A) - 1]$, where [B] is the concentration of antagonist, A' and A the $EC_{50}$ values of agonist measured respectively in the presence and in the absence of antagonist (Furchgott, 1972).

| DRUG | $EC_{50}$ (nM) | $E_{max}$* (% 5-HT RESPONSE) | $K_B$ (nM) | INTRINSIC ACTIVITY |
|---|---|---|---|---|
| 5-CT | 17 ± 2 | 110 ± 19 | | AGONIST |
| 5-MeO-T | 173 ± 1 | 100 ± 5 | | AGONIST |
| 5-HT | 189 ± 17 | 100 | | AGONIST |
| DP-5-CT | 2,398 ± 49 | 86 ± 12 | | AGONIST |
| 8-OH-DPAT | 17,160 ± 1,254 | 51 ± 14 | | PARTIAL AGONIST |
| d-LSD | | 0 | 2.7 ± 0.5 | ANTAGONIST |
| Methiothepin | | 0 | 11 ± 1 | ANTAGONIST |
| 2-Br-LSD | | 0 | 12 ± 3 | ANTAGONIST |
| DHE | | 0 | 20 ± 4 | ANTAGONIST |
| Mesulergine | | 0 | 20 ± 1 | ANTAGONIST |
| Bromocriptine | | 0 | 240 ± 10 | ANTAGONIST |

Discussion

We have cloned DNA representing a novel human serotonin receptor (hp78a or $5HT_{4B}$.) from, human brain cDNA and genomic DNA. Of all known G protein-coupled receptor sequences (EMBL/Genbank Data Base), the greatest homology was between clone hp78a receptor gene and the Drosophila 5HTR serotonin receptor gene (Witz et al., 1990). Comparison of clone hp78a deduced amino acid sequence with known G protein-coupled receptor sequences indicates the greatest concentration of identical amino acids to be in the transmembrane domains. In these TM regions, the percentage of identity for hp78a clone is 57% compared to Dro5HTR1, 39–53% with serotonin receptor subfamily (see FIGS. 2-1–2-4), 40–50% with adrenergic receptor subfamily, 44–49% with the dopamine receptor subfamily, 37–41% with histamine receptor subfamily, 27–28% with peptide receptors and 32–33% with adensine receptors. Both the alignment and percent identity of this human hp78a sequence, relative to other G protein-coupled receptors or other members of the serotonergic subfamily, strongly suggest that this is a new receptor. Because the TM homology between the clone hp78a receptor and any of the known serotonin receptors is below 55% and the fact that this receptor is positively-coupled to adenylate cyclase (see RESULTS and below), we are naming this clone $5HT_{4B}$.

Localization of transcripts for this receptor indicate a relatively broad tissue distribution. Of the tissues examined, the human 5-HT4B (clone hp78a) receptor mRNA was detected in greatest abundance in the brain, testes and bladder, with moderate to low levels found in other peripheral tissues, with no signal detected in skin and tongue.

The distribution of the $5\text{-}HT_{4B}$ receptor and its mRNA, described herein, indicates that this novel serotonin receptor may subserve functions within several brain systems. The limbic system (septum, centromedial amygdala, anterior hippocampal rudiment, hypothalamus) is particularly well-represented, suggesting a role for the $5\text{-}HT_{4B}$ receptor in affective processes. The finding that this receptor binds clozapine very well supports this notion, intimating that the $^5\text{-}HT_{4B}$ receptor may be involved in schizophrenia or in other neurologically based affective disorders. In addition, the localization of the clone hp78a mRNA to thalamic nuclei which project to neocortex suggests that this receptor is involved in sensory processes. The localization in the raphe nuclei indicate possible function as autoreceptors which can be targeted as novel therapies through $5\text{-}HT_{4B}$ function in anxiolytics or antidepressants. Since the distribution of 5-HT receptors is generally preserved across species, the localization results from non-human species, such as rat or guinea pig, are considered most likely analogous to human brain.

The binding profile obtained with the clone hp78a receptor appears to represent a distinct serotonin receptor subtype based upon its unique pharmacological profile. The rank order of compounds to displace $[^3H]$5-HT binding (Table 3) does not match the binding properties obtained with other $[^3H]$5-HT labeled binding sites (Xiong and Nelson, 1989; Zemlin et al., 1991) or pharmacological properties of pharmacologically defined serotonin receptors described in a variety of functional preparations (see below). The high affinity of 5-CT ($K_i=0.5$ nM) and low affinity of sumatriptan ($K_i>750$ nM) for the clone hp78a receptor matches the binding properties of a $[^3H]$5-CT binding site recently identified in guinea pig striatal homogenates (Mahle et al., 1992). However, a direct comparison of the pharmacological properties of the clone hp78a receptor to that of the $[^3H]$5-CT binding site cannot be made since a complete characterization of the binding site is lacking and no functional response has been demonstrated.

Binding criteria used to classify $5\text{-}HT_1$ receptor subtypes include high affinity for 5-HT and 5-CT. These two compounds exhibited high affinity for the clone hp78a receptor (Table 3). However, both the recently cloned human $5\text{-}HT_{1E}$ (McAllister et al., 1992; Zgombick et al., 1992) and $5\text{-}HT_{1F}$ (Adham et al., 1992) receptors display high affinity for 5-HT ($K_i<10$ nM) and low affinity for 5-CT ($K_i>700$ nM). The $5\text{-}HT_{1E}$ and $5\text{-}HT_{1F}$ receptors are members of the $5\text{-}HT_1$ receptor family based upon their TM homologies to that of other cloned members of this receptor family ($5\text{-}HT_{1A}$, $5\text{-}HT_{1B}$, $5\text{-}HT_{1D\alpha}$, $5\text{-}HT_{1D\beta}$) and second messenger coupling (inhibition of adenylate cyclase). Moreover, while the cloned $5\text{-}HT_{1C}$ receptor binds $(^3H]$5-HT with high affinity, it is considered a $5\text{-}HT_2$ receptor based upon it high TM homology (75%) to the cloned $5\text{-}HT_2$ receptor and functional coupling to phospholipase C (Hartig et al., 1990; Julius, 1992). Based upon these observations, it is difficult to classify clone hp78a receptor as a $5\text{-}HT_1$ receptor subtype based solely on its radioligand binding properties.

Functional responses of the clone hp78a receptor provide additional insight into its identity. The clone hp78a receptor gene transiently expressed in Cos-7 cells coupled to stimulation of adenylate cyclase. Both 5-HT and 5-CT elicited a 20-fold increase in cAMP release over basal levels. The $K_i$ values 5-HT and 5-CT obtained in binding assays were approximately 100-fold higher affinity than the $EC_{50}$ values of these agonists obtained from functional assays. The rank order of potency of agonists observed in the functional assay 5-CT>5-HT≧5-MeOT>8-OH-DPAT is very similar to the rank order of these compounds to displace specific $[^3H]$5-HT binding. Stable LM(tk$^-$) cells expressing the $5\text{-}HT_{4B}$ receptor gave very similar pharmacology to the transiently transfected COS-7 cells with agonists producing essentially identical rank order of potencies, however the maximum cAMP response produced by agonists was lower in LM(tk$^-$) cells. Antagonists had the following rank order of potencies: d-LSD>methiothepin≧2-Br-LSD>mesulergine=DHE.

The ability of serotonin to activate adenylate cyclase has been demonstrated in several systems including: embryonic mouse colliculi (5-HT$_4$, Dumius et al., 1988), horse brain glial membranes (5-HT$_1$-like, Fillion et al., 1980), rat and guinea-pig hippocampal membranes (5-HT$_{TA}$, Shenker et al., 1987), human atria (5-HT$_4$, Kaumann et al., 1989), NCB20 neuroblastoma hybrid cells (5-HT$_4$-like, Conner and Mansour, 1990; Cossery et al., 1990) and neonatal porcine vena cava (5-HT$_1$-like, Trevethick et al., 1984). The receptor encoded by HT$_{4B}$ gene is distinct from the 5-HT$_4$ receptor identified in these preparations, although there are some common properties. Both the 5-HT$_4$ receptors found in the colliculi, atria and on the NCB20 cells and clone hp78a receptor have equipotency for 5-HT and 5-MeOT which stimulate cAMP release with low affinity. In addition, they are both relatively insensitive to 8-OH-DPAT, spiperone, ketanserin, and pindolol. However, methiothepin is a potent antagonist of the functional responses mediated by clone hp78a receptor but not of the colliculi and atrial 5-HT$_4$ receptor responses. Most critically, compounds used to define the "classical" 5-HT$_4$ receptor (agonists: cisapride, zacopride, BRL 29429; weak antagonist: ICS-205-930) are all either poorly active or inactive at the clone hp78a receptor.

A somewhat closer pharmacological relationship exists between the clone hp78a receptor and the 5-HT4-like receptor on NCB20 cells, including the potent antagonist activity of methiothepin. However, they are distinct entities based on the following differences: a) [$^3$H]-5-HT binds with high affinity (Kd=8.5 nM) to clone hp78a receptor but it has a very low affinity (~200 nM) at the 5-HT receptors on NCB20 cells (Berry-Kravis and Dawson, 1983), b) the rank order of potency of agonists at hp78a is 5-CT>5-HT≧5-MeoT, whereas on NCB20 cells the order is 5-HT≧5-MeOT>5-CT (Conner and Mansour, 1990). In addition, clone hp78a receptor share several properties with the 5-HT receptor present in glial membranes (Fillion et al., 1980) These include: (a) the equilibrium dissociation constant of [$^3$H]-5-HT, $K_d$=10 Nm; (b) the $EC_{50}$ value for 5-HT stimulation of cAMP (500–1000 nM, and (c) Potent antagonism by: 2-bromoLSD, methysergide and methiothepin.

Criteria used to classify serotonin receptors into four distinct classes designated 5-HT$_1$, 5-HT$_2$, 5-HT$_3$, and 5-HT$_4$ is based upon binding properties, signal transduction mechanisms, and deduced amino acid sequences. According to the serotonin receptor classification scheme proposed by Bradley et al., (1986), clone hp78a receptor could be considered a member of the 5-HT$_1$ receptor family since 5-CT behaves as an agonist and this response is potently antagonized by the nonselective 5-HT$_1$ antagonist methiothepin. However, the positive coupling of clone hp78a receptor to adenylate cyclase seen here is not consistent with that reported for cloned members of 5-HT$_1$ receptor subfamily which couple to the inhibition of FSK-stimulation cAMP release and include the 5-HT$_{1A}$ (Kobilka et al., 1987; Fargin et al., 1988), 5-HT$_{1B}$ (Adham et al., 1992; Maroteaux et al., 1992), 5-HT$_{1D\alpha}$(Hamblin and Metcalf, 1991: Weinshank et al., 1992); 5-HT$_{1D\beta}$(Demchyshyn et al., 1992; Jin et al., 1992; Weinshank et al., 1992); 5-HT$_{1E}$ (Levy et al., 1992; McAllister et al., 1992; Zgombick et al., 1992); and 5-HT$_{1F}$ (Adham et al., submitted).

Although a useful construct, classification of serotonin receptors based solely on binding properties can be misleading. For example, the 5-HT$_{1C}$ receptor, named originally by binding criteria, ([$^3$H]5-HT binds with high affinity to the this subtype) is now considered a 5-HT$_2$ subtype based upon the high degree (75%) homology within the TM domains to the 5-HT$_2$ receptor and second messenger coupling (phosphoinositide hydrolysis) [Hartig et al., 1990; Julius, 1992]. Similarly, although the clone hp78a receptor binds [$^3$H]5-HT with high affinity, its positive coupling to adenylate cyclase and the lower TM homology (~50%) to other cloned members of the 5-HT$_1$ receptor family would seem to exclude the possibility clone hp78a encodes a 5-HT$_1$ subtype. Thus, it appears that TM homology comparisons and second messenger coupling are more accurate predictors for receptor classification than radioligand binding properties. Based upon these analyses, we propose that clone hp78a be designated the first member of the 5-HT$_4$ receptor subfamily. The pharmacological profile of clone hp78a is distinct from that of the pharmacologically defined 5-HT$_4$ receptor. Therefore, clone hp78a will be termed 5-HT$_{4B}$, reserving the 5-HT$_{4A}$ designation for a clone which will display the pharmacological profile of the 5-HT$_4$ receptor described in a variety of isolated tissue preparations (Bokaert et al, 1992).

In conclusion, the primary structure of the hp78a gene, as well as its unique pharmacological profile and positive coupling to adenylate cyclase obtained from transiently transfected cells, indicate that this gene may encode the first member of the 5-HT$_4$ receptor family. Clone hp78a is proposed to be designated as the 5-HT$_{4B}$ receptor subtype since it does not display the pharmacological properties of the pharmacologically defined 5-HT$_4$ receptor. Additional cloning efforts will be required to isolate additional members of this newly recognized serotonin receptor family (Bockaert et al., 1992). Comparison of the pharmacological relationship of 5-HT$_{4B}$ with serotonin receptors defined in tissue models indicates a possible identity with a collection of related receptors described in the vasculature. Several of these receptors appear to underlie relaxant responses in isolated blood vessels indicating potential therapeutic benefit in angina, coronary artery disease, atherosclerosis, and possibly cerebral blood vessel disorders leading to stroke. The presence of this subtype in the CNS also indicates potential use in disorders of higher cognitive processes as well as control of autonomic function. Moreover, the relatively high affinity ($K_i$=78 nM) of the atypical antipsychotic clozapine for the 5-HT$_7$ receptor, as well as the localization of this subtype in limbic and cortical regions, indicates a potential role of the 5-HT$_7$ subtype in neuropsychiatric disorders such as schizophrenia which involve serotonergic neurotransmission.

REFERENCES

Adham, N., H.-T. Kao, L. E. Schechter, J. Bard, M. Olsen, D. Urquhart, M. Durkin, P. R. Hartig, R. L. Weinshank, and T. Branchek. Cloning of a novel human serotonin receptor (5-HT1F): A fifth 5-HT$_1$ receptor subtype coupled to the inhibition of adenylate cyclase. Submitted.

Berry-Kravis, E., and G. Dawson. Characterization of an adenylate cyclase-linked serotonin (5-HT$_1$) receptor in a neuroblastoma X brain explant hybrid cell line (NCB-20). J. Neurochem. 40:977–985 (1983).

Bockaert, J., J. R. Fozard, A. Dumuis, D. E. Clarke. The 5-HT4 receptor: a place in the sun. Trends Pharmacol. Sci. 13:141–145 (1992).

Bockaert, J., M. Sebben, and A. Dumius. Pharmacological characterization of 5-hydroxytryptamine$_4$ (5-HT$_4$) receptors positively coupled to adenylate cyclase in adult guinea-pig hippocampal membranes: Effect of substituted benzamide derivatives. Mol. Pharmacol. 37:408–411.

Bradford, M. M. A rapid and sensitive method for the quantification of microgram quantities of protein utilizing the principle of protein-dye binding. Anal. Biochem. 72:248–254 (1976).

Bradley, P. B., G. Engel., w. Fenuik, J. R. Fozard, P. P. Humphrey et al. Proposals for the nomenclature of functional receptors for 5-hydroxytryptamine. Neuropharmacology 25:563–576 (1986).

Branchek, T., N. Adham, M. Macchi, H.-T. Kao, and P. R. Hartig. [$^3$H]-DOB (4-bromo-2,5-dimethoxyphenylisopropylamine) and [$^3$H]ketanserin label two affinity states of the cloned human 5-hydroxytryptamine$_2$ receptor. Mol. Pharmacol. 38:604–609 (1990).

Cheng, Y. C., and W. H. Prusoff. Relationship between the inhibition constant ($K_i$) and the concentration of the inhibitor which causes 50 per cent inhibition ($IC_{50}$) of an enzyme reaction. Biochem. Pharmacol. 22:3099–3108 (1973).

Connor, D. A., and T. E. Mansour. Serotonin receptor-mediated activation of adenylate cyclase in neuroblastoma NCB-20: a novel 5-hydroxytryptamine receptor. Mol. Pharmacol. 37:742–751 (1990).

Cossery, J. M., J.-M. Mienville, P. A. Sheehy, A. M. Mellow, and D.-M. Chuang. Characterization of two distinct 5-HT receptors coupled to adenylate cyclase activation and ion current generation in NCB-20 cells. Neurosci. Lett. 108:149–154 (1990).

Cushing, D. and Cohen, M. L. Comparison of the serotonin receptors that mediate smooth muscle contraction in canine and porcine coronary artery. J. Pharmacol. Exp. The. 261: 856–861, 1992.

Demchyshyn, L., R. K. Sunahara, K. Miller, M. Teitler, B. J. Hoffman, J. L. Kennedy, P. Seeman, H. H. M. Van Tol, and H. B. Niznik. A human serotonin 1D receptor variant (5-HT1Dα) encoded by an intronless gene on chromosome 6. Proc. Natl. Acad. Sci. USA 89:5522–5526 (1992).

Dumuis, A., R. Bouhelal, M. Sebben, R. Cory, and J. Bockaert. A nonclassical 5-hydroxytryptamine receptor positively coupled with adenylate cyclase in the central nervous system. Mol. Pharmacol. 34:880–887 (1988).

Fargin, A., J. R. Raymond, J. R. Regan, S. Cotecchia, R. J. Lefkowitz, and M. G. Caron. Effector coupling mechanisms of the cloned 5-HT1A receptor. J. Biol. Chem. 264:14848–14852 (1989).

Fillion G., D. Beaudoin, J. C. Rousselle, and J. Jacob. [$^3$H]5-HT binding sites and 5-HT-sensitive adenylate cyclase in glial cell membrane fraction. Brain Res. 198:361–374 (1980).

Foquet, M., D. Hoyer, L. A. Pardo, A. Parekh, F. W. Kluxen, H. O. Kalkman, W. Stühmer, and H. Lübbert. Cloning and functional characterization of the rat stomach fundus serotonin receptor. EMBO J. 11(3):3481–3487 (1992).

Frazier, A., S. Maayani, and B. B. Wolfe. Subtypes of receptors for serotonin. Ann. Rev. Pharmacol. Toxicol. 30:307–348 (1990).

Furchgott, R. F. The classification of adrenoceptors (adrenergic receptors). An evaluation from the standpoint of receptor theory, in Catecholamines (H. Blaschko, and E. Muscholl, eds.). Springer Press, Berlin, Heidelberg, New York and Tokyo, 283–335 (1972).

Hamblin, M. W., and M. A. Metcalf. Primary structure and functional characterization of a human 5-$HT_{1D}$-type serotonin receptor. Mol. Pharmacol. 40:143–148 (1991).

Hartig, P. R. TIPS 10:64–69 (1989).

Hartig, P. R., H.-T. Kao, M. Macchi, N. Adham, J. Zgombick, R. Weinshank, and T. Branchek. The molecular biology of serotonin receptors: an overview. Neuropsychopharmacol. 3:335–347 (1990).

Jin, H., D. Oskenberg, A. Askenazi, S. Peroutka, A. M. V. Duncan, R. Rozmahel, Y. Yang, G. Mengod, J. Palacios, B. O'Dowd. J. Biol. Chem. 267: 5736–5738 (1992)

Julius, D., A. B. MacDermott, R. Axel, T. Jessel. Molecular characterization of a functional cDNA encoding the serotonin 1c receptor. Science 241:558–564 (1988).

Julius, D. Molecular biology of serotonin receptors. Ann. Rev. Neurosci. 14:335–360 (1991).

Kingston, R. E., In: Current Protocols in Molecular Biology, Vol. I (John Wiley and Sons, N.Y.), 1987.

Levy, F. O., T. Gudermann, M. Birnbaumer, A. J. Kaumann, and L. Birnbaumer. Molecular cloning of a human gene (S31) encoding a novel serotonin receptor mediating inhibition of adenylyl cyclase. FEBS. Lett. 296:201–206 (1992).

Lübbert, H., T. P. Snutch, N. Dascal, H. A. Lester, and N. Davidson. Rat brain 5-$HT_{1C}$ receptors are encoded by a 5–6 kbase mRNA size class and are functionally expressed in injected Xenopus oocytes. J. Neurosci. 7:1159–1165 (1987).

Mahle, C. D., H. P. Nowak, R. J. Mattson, S. D. Hurt, and F. D. Yocca. [$^3$H]5-Carboxamidotryptamine labels multiple high affinity 5-$HT_{1D}$-like sites in guinea pig brain. Eur. J. Pharmacol. 205:323–324 (1991).

Maricq, A. V., A. V. Peterson, A. J. Brake, R. M. Myers, and D. Julius. Primary structure and functional expression of the 5-HT3 receptor, a serotonin-gated ion channel. Science 254:432–436 (1991).

Maroteaux, L., F. Saudou, N. Amlaiky, U. Boschert, J. L. Plassat, R. Hen. Mouse 5-HT1B serotonin receptor: cloning, functional expression, and localization in motor control centers. Proc. Natl. Acad. Sci. 89:3020–3024 (1992).

McAllister, G., A. Charlesworth, C. Snodin, M. S. Beer, A. J. Noble, D. N. Middlemiss, L. L. Iverson, and P. Whiting. Molecular cloning of a serotonin receptor from human brain (5-HT1E); A fifth 5-HT1-like subtype. Proc. Natl. Acad. Sci. USA 89:5517–5521, 1992

Miller, J., and R. N. Germain. Efficient cell surface expression of class II MHC molecules in the absence of associated invariant chain. J. Exp. Med. 164:1478–1489 (1986).

Mylecharane, E. and Phillips, C. Mechanisms of 5-hydroxytryptamine-induced vasodilation. In: The Peripheral Actions of 5-hydroxytryptamine, J. R. Fozard, ed. Oxford University Press, Oxford, pp. 147–181 (1989).

Pritchett, D. B., A. W. J. Bach, M. Wozny, O. Taleb, R. Dal Toso, J. C. Shih, and P. H. Seeburg. Structure and functional expression of a cloned rat serotonin 5-HT-2 receptor. EMBO J. 7:4135–4140 (1988).

Sambrook, J., Fritsch, E. F., and Maniatis, T., In: Molecular Cloning: A Laboratory Manual, 2nd Edition (Cold Spring Harbor Laboratory, Cold Spring Harbor, N.Y.), 1989.

Sanger, F., Nicklen, S. and Coulsen, A. R. Proc. Natl. Acad. Scd. USA 74:5463–5467 (1977).

Savarese, T. M. and Fraser, L. M. Biochem. J. 283:1–19 (1992)

Shenker, A., S. Maayani, H. Weinstein, and J. P. Green, Pharmacological characterization of two 5-hydroxytryptamine receptors coupled to adenylate cyclase in guinea pig hippocampal membranes. Mol. Pharmacol. 31:357–367 (1987).

Southern, E. M. J. Mol. Biol. 98:503–517 (1975).

Trevethick, M. A., W. Feniuk, and P. P. A. Humphrey. 5-hydroxytryptamine induced relaxation of neonatal porcine vena cava in vitro. Life Sci. 35:477–486 (1984).

Weinshank, R. L., Zgombick, J. M., Macchi, M., Adham, N., Lichtblau, H., Branchek, T. A. and Hartig, P. R. Mol. Pharmacol. 38:681–688 (1990).

Weinshank, R. L., J. M. Zgombick, M. Macchi, T. A. Branchek, and P. R. Hartig. The human serotonin 1D receptor is encoded by a subfamily of two distinct genes: 5-$HT_{1D\alpha}$ and 5-$HT_{1D\beta}$. Proc. Natl. Acad. Sci. (USA) 89:3630–3634 (1992a).

Weinshank, R. L., Adham, N., Zgombick, J., Bard, J., Branchek, T. and Hartig, P. R., In: Serotonin Receptor Subtypes: Pharmacological Significance and Clinical Implications, Vol. I. Int. Acad. Biomed. Drug Res. (S. Krager, Basel, Switzerland), (1992b).

Witz, P., Amlaiky, N., Plassat, J.-L., Maroteaux, L., Borrelli, E. and Hen, R. Proc. Natl. Acad. Sci. USA 87:8940–8944 (1990).

Zemlan, F. P., and E. F. Schwab. Characterization of a novel serotonin receptor subtype (5-$HT_{1S}$) in rat CNS: interaction with a GTP binding protein. J. Neurochem. 57:2092–2099 (1991).

Zgombick, J. M., R. L. Weinshank, M. Macchi, L. E. Schechter, T. A. Branchek, and P. R. Hartig. Expression and pharmacological characterization of a canine 5-hydroxytryptamine$_{1D}$ receptor subtype. Mol. Pharmacol. 40: 1036–1042 (1991).

Zgombick, J. M., L. E. Schechter, M. Macchi, P. R. Hartig, T. A. Branchek, and R. L. Weinshank. Human gene S31 encodes the pharmacologically defined serotonin 5-hydroytryptamine$_{1E}$ receptor. Mol. Pharmacol. (1992), in press.

What is claimed is:

1. A process for identifying a chemical compound which specifically binds to a human 5-HT$_{4B}$ receptor, which comprises contacting nonneuronal cells expressing on their cell surface the human -5-HT$_{4B}$ receptor encoded by the nucleotide coding sequence shown in FIGS. 1-1 to 1-5 beginning at the A at position 1 and ending at the T at position 1336 (SEQ ID NO: 1), with the chemical compound under conditions suitable for binding, and detecting specific binding of the chemical compound to the human 5-HT$_{4B}$ receptor.

2. A process for identifying a chemical compound which specifically binds to a human 5-HT$_{4B}$ receptor, which comprises contacting a membrane fraction from a cell extract of nonneuronal cells expressing on their cell surface the human 5-HT$_{4B}$ receptor encoded by the nucleotide coding sequence shown in FIGS. 1-1 to 1-5 beginning at the A at position 1 and ending at the T at position 1335 (SEQ ID NO: 1), with the chemical compound under conditions suitable for binding, and detecting specific binding of the chemical compound to the human 5-HT$_{4B}$ receptor.

3. A process involving competitive binding for identifying a chemical compound which specifically binds to a human 5-HT$_{4B}$ receptor, which comprises separately contacting nonneuronal tells expressing on their cell surface the human 5HT$_{4B}$ receptor encoded by the nucleotide coding sequence shown in FIGS. 1-1 to 1-5 beginning at the A it position 1 and ending at the T at position 1336 (SEQ ID NO: 1), with both the chemical compound and a second chemical compound known to bind to the human 5-HT$_{4B}$ receptor, and with only the second chemical compound, under conditions suitable for binding of both compounds, and detecting specific binding of one chemical compound to the human 5-HT$_{4B}$ receptor, a decrease in binding of the second chemical compound to the human 5-HT$_{4B}$ recepor in the presence of the chemical compound indicating that the chemical compound binds to the human 5-HT$_{4B}$ receptor.

4. A process involving competictive binding for identifying a chemical compound which specifically binds to th human 5-HT$_{4B}$ receptor, which comprises separately contacting a membrane fraction from a cell extract of nonneuronal cells expressing on their cell surface the human 5-HT$_{4B}$ receptor encoded by the nucleotide coding sequence shown in FIGS. 1-1 to 1-5 beginning at the A at position 1 and ending at the T at position 1336 (SEQ ID NO: 1), with both the chemical compound and a second chemical compound known to bind to the human 5-HT$_{4B}$ receptor, and with only the second chemical compound, under conditions suitable for binding of both compounds, and detecting specific binding of the chemical compound to the human 5-HT$_{4B}$ receptor, a decrease in binding of the second chemical compound to the human 5-HT$_{4B}$ receptor in the presence of the chemical compound indicating that the chemical compound binds to the human 5-HT$_{4B}$ receptor.

5. A process for determining whether a chemical compound specifically binds to and activates a human 5-HT$_{4B}$ receptor, which comprises contacting nonneuronal cells introducing a second messenger response and expressing on their cell surface the human 5-HT$_{4B}$ receptor encoded by the nucleotide coding sequence shown in FIGS. 1-1 to 1-5 beginning at the A at position 1 and ending at the T at position 1336 (SEQ ID NO: 1), with the chemical compound under conditions suitable for activation of the human 5-HT$_{4B}$ receptor, and measuring the second messenger response in the presence and in the absence of the chemical compound, a change in second messenger response in the presence of the chemical compound indicating that the chemical compound activates the human 5-HT$_{4B}$ receptor.

6. A process for determining whether a chemical compound specifically binds to and activates a human 5-HT$_{4B}$ receptor, which comprises contacting a membrane fraction from a cell extract of nonneuronal cells producing a second messenger response and expressing on their cell surface the human 5-HT$_{4B}$ receptor encoded by the nucleotide coding sequence shown in FIGS. 1-1 to 1-5 beginning at the A at position 1 and ending at the T at position 1336 (SEQ ID NO: 1), with the chemical compound under conditions suitable for activation of the human 5-HT$_{4B}$ receptor, and measuring the second messenger response in the presence and in the absence of the chemical compound, a change in second messenger response in the presence of the chemical compound indicating that the chemical compound activates the human 5-HT$_{4B}$ receptor.

7. A process for determining whether a chemical compound specifically binds to and inhibits activation of a human 5-HT$_{4B}$ receptor, which comprises separately contacting nonneuronal cells producing a second messenger response and expressing on their cell surface the human 5-HT$_{4B}$ receptor encoded by the nucleotide coding sequence shown in FIGS. 1-1 to 1-5 beginning at the A at position 1 and ending at the T at position 1336 (SEQ ID NO: 1), with both the chemical compound and a second chemical compound known to activate the human 5-HT$_{4B}$ receptor, and with only the second chemical compound, under conditions suitable for activation of the human 5-HT$_{4B}$ receptor, and measuring the second messenger response in the presence of only the second chemical compound and in the presence of both the second chemical compound and the chemical compound, a smaller change in second messenger response in the presence of both the chemical compound and the second chemical compound than in the presence of only the second chemical compound indicating that the chemical compound inhibits activation of the human 5-HT$_{4B}$ receptor.

8. A process for determining whether a chemical compound specifically binds to and inhibits activation of a human 5-HT$_{4B}$ receptor, which comprises separately contacting a membrane fraction from a cell extract of nonneuronal cells producing a second messenger response and expressing on their cell surface the human 5-HT$_{4B}$ receptor encoded by the nucleotide coding sequence shown in FIGS. 1-1 to 1-5 beginning at the A at position 1 and ending at the T at position 1336 (SEQ ID NO: 1), with both the chemical compound and a second chemical compound known to activate the human 5-HT$_{4B}$ receptor, and with only the second chemical compound, under conditions suitable for activation of the human 5-HT$_{4B}$ receptor, and measuring the second messenger response in the presence of only the second chemical compound and in the presence of both the second chemical compound and the chemical compound, a smaller change in second messenger response in the presence of both the chemical compound and the second chemical compound than in the presence of only the second chemical compound indicating that the chemical compound inhibits activation of the human 5-HT$_{4B}$ receptor.

9. The process of claim 5 or 6, wherein the second messenger response comprises adenylate cyclase activity and the change in second messenger response is an increase in adenylate cyclase activity.

10. The process of claim 7 or 8, wherein the second messenger response comprises adenylate cyclase activity and the change in the second messenger response is a smaller increase in the level of adenylate cyclase activity in the presence of both the chemical compound and the second chemical compound than in the presence of only the second chemical compound.

11. The process of any one of claims 1, 2, 3, 4, 5, 6, 7, or 8, wherein the nonneuronal cell is a mammalian cell.

12. The process of claim 11, wherein the mammalian cell is a NIH 3T3 cell, a LM(tk–) cell, a COS 7 cell or a Chinese hamster ovary (CHO) cell.

* * * * *

UNITED STATES PATENT AND TRADEMARK OFFICE
CERTIFICATE OF CORRECTION

PATENT NO. : 6,300,087 B1
DATED : October 9, 2001
INVENTOR(S) : Jonathan A. Bard et al.

It is certified that error appears in the above-identified patent and that said Letters Patent is hereby corrected as shown below:

Title page,
Item [62], Related U.S. Application Data, "Continuation of U.S. Ser. No. 09/332,837, filed Jun. 14, 1999, which is a continuation of application No. 08/157,185, filed as application No. PCT/US93/10553, filed Oct. 29, 1993, now Pat. No. 5,985,585, which is a continuation-in-part of application No. 07/971,690, filed Nov. 3, 1992, now abandoned, and a continuation-in-part of application No. 08/281,526, filed Jul. 27, 1994, now U.S. Pat. No. 6,083,749." should read -- Continuation of U.S. Ser. No. 09/332,837, filed Jun. 14, 1999, which is a continuation of U.S. Ser. No. 08/157,185, filed Jun. 15, 1995, now U.S. Pat. No. 5,985,585, issued Nov. 16, 1999, which was both a §371 national stage filing of PCT International Application No. PCT/US93/10553, filed Oct. 29, 1993, which claims priority of and was a continuation-in-part of U.S. Ser. No. 07/971,690, filed Nov. 3, 1992, now abandoned, and a continuation-in-part of U.S. Ser. No. 08/281,526, filed Jul. 27, 1994, now U.S. Pat. No. 6,083,749, issued Jul. 4, 2000. --.

Column 1,
Line 66, "[Cushing and Cohen, 1992" should read -- (Cushing and Cohen, 1992) --.

Column 2,
Line 37, "5-HT4B" should read -- $5\text{-}HT_{4B}$ --.
Line 44, "$5\text{-}HT^{4B}$" should read -- $5\text{-}HT_{4B}$ --.

Column 3,
Line 1, "5-HT4B" should read -- $5\text{-}HT_{4B}$ --.
Line 22, "$^5\text{-}HT_{4B}$" should read -- $5\text{-}HT_{4B}$ --.
Line 53, "$5\text{-}HT^{4B}$" should read -- $5\text{-}HT_{4B}$ --.

Column 4,
Line 65, "5-HT4B" should read -- $5\text{-}HT_{4B}$ --.
Line 67, "5-HT4B" should read -- $5\text{-}HT_{4B}$ --.

Column 6,
Line 27, "(Sequence I.D. No. 1)" should read -- SEQ ID NO: 1 --.
Line 38, "FIG. 1" should read -- FIGS. 1-1-1-5 --.
Line 41, "$^5\text{-}HT_{4B}$" should read -- $5\text{-}HT_{4B}$ --.

Column 8,
Line 22, "$^5\text{-}HT_{4B}$" should read -- $5\text{-}HT_{4B}$ --.
Line 45, "FIGS. 1-1-1=" should read -- FIGS 1-1-1-5 --.

Column 9,
Line 44, "mA" should read -- mRNA --.

UNITED STATES PATENT AND TRADEMARK OFFICE
CERTIFICATE OF CORRECTION

PATENT NO.   : 6,300,087 B1
DATED        : October 9, 2001
INVENTOR(S)  : Jonathan A. Bard et al.

It is certified that error appears in the above-identified patent and that said Letters Patent is hereby corrected as shown below:

Column 11,
Lines 47 and 57, "FIGS. 1-1-1=" should read -- FIGS 1-1-1-5 --.

Column 12,
Line 3, "FIGS. 1-1-1=" should read -- FIGS 1-1-1-5 --.
Line 30, "5-$HT_4$" should read -- 5-$HT_{4B}$ --.

Column 13,
Line 1, "S-$HT_{4B}$" should read -- 5-$HT_{4B}$ --.

Column 15,
Line 4, "$^5$-$HT_{4B}$" should read -- 5-$HT_{4B}$ --.
Line 13, "FIGS. 1-1-1=" should read -- FIGS 1-1-1-5 --.

Column 16,
Line 12, "FIGS. 1-1-1=" should read -- FIGS 1-1-1-5 --.
Line 27, "$^5$-$HT_{4B}$" should read -- 5-$HT_{4B}$ --.
Line 31, "a- $HT_{4B}$" should read -- 5-$HT_{4B}$ --.

Column 20,
Line 10, "($\alpha$-$^{32}$P]dATP" should read -- [$\alpha$-$^{32}$P]dATP --.
Line 16, "3" should read -- 3' --.

Column 25,
Line 35, "$dH_{20}$" should read -- $dH_2O$ --.

Column 27,
Line 19, "[$^3$H)5-HT" should read -- [$^3$H]5-HT --.

UNITED STATES PATENT AND TRADEMARK OFFICE
CERTIFICATE OF CORRECTION

PATENT NO. : 6,300,087 B1
DATED : October 9, 2001
INVENTOR(S) : Jonathan A. Bard et al.

It is certified that error appears in the above-identified patent and that said Letters Patent is hereby corrected as shown below:

Column 31,
Line 31, "5-HT4B" should read -- $5\text{-}HT_4$ --.
Line 43, "$^5\text{-}HT_{4B}$" should read -- $5\text{-}HT_{4B}$ --.

Signed and Sealed this

Thirteenth Day of June, 2006

JON W. DUDAS
*Director of the United States Patent and Trademark Office*